US011207350B2

(12) United States Patent
Lee et al.

(10) Patent No.: US 11,207,350 B2
(45) Date of Patent: *Dec. 28, 2021

(54) GENETICALLY MODIFIED NK-92 CELLS AND MONOCLONAL ANTIBODIES FOR THE TREATMENT OF CANCER

(71) Applicant: NantKwest, Inc., San Diego, CA (US)

(72) Inventors: Tien Lee, San Diego, CA (US); Hans G. Klingemann, San Diego, CA (US); Barry J. Simon, San Diego, CA (US); Laurent Boissel, San Diego, CA (US)

(73) Assignee: ImmunityBio, Inc., San Diego, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 17/217,839

(22) Filed: Mar. 30, 2021

(65) Prior Publication Data

US 2021/0236550 A1  Aug. 5, 2021

Related U.S. Application Data

(63) Continuation of application No. 16/903,882, filed on Jun. 17, 2020, now Pat. No. 11,000,550, which is a continuation of application No. 16/541,847, filed on Aug. 15, 2019, now Pat. No. 10,736,921, which is a continuation of application No. 15/529,848, filed as application No. PCT/US2016/024318 on Mar. 25, 2016, now Pat. No. 10,456,420.

(60) Provisional application No. 62/139,258, filed on Mar. 27, 2015.

(51) Int. Cl.
```
A61K 35/17      (2015.01)
C07K 16/28      (2006.01)
C12N 5/0783     (2010.01)
A61K 39/395     (2006.01)
C07K 16/32      (2006.01)
A61K 39/00      (2006.01)
```

(52) U.S. Cl.
CPC ........ *A61K 35/17* (2013.01); *A61K 39/39558* (2013.01); *C07K 16/2803* (2013.01); *C07K 16/2827* (2013.01); *C07K 16/2887* (2013.01); *C07K 16/32* (2013.01); *C12N 5/0646* (2013.01); *A61K 2039/5156* (2013.01); *A61K 2039/572* (2013.01); *A61K 2300/00* (2013.01); *C07K 2317/24* (2013.01); *C07K 2317/732* (2013.01); *C12N 2501/2302* (2013.01); *C12N 2501/48* (2013.01); *C12N 2501/599* (2013.01); *C12N 2501/727* (2013.01); *C12N 2510/00* (2013.01)

(58) Field of Classification Search
None
See application file for complete search history.

(56) References Cited

U.S. PATENT DOCUMENTS

| | | | |
|---|---|---|---|
| 7,351,803 B2 | 4/2008 | Johnson | |
| 7,618,817 B2 | 11/2009 | Campbell | |
| 8,313,943 B2 | 11/2012 | Campbell | |
| 9,150,636 B2 | 10/2015 | Campbell | |
| 9,181,322 B2 | 11/2015 | Campbell | |
| 10,456,420 B2 * | 10/2019 | Lee | C07K 16/32 |
| 10,736,921 B2 * | 8/2020 | Lee | C07K 16/2827 |
| 11,000,550 B2 * | 5/2021 | Lee | C07K 16/2887 |
| 2006/0029583 A1 | 2/2006 | Dilber et al. | |
| 2006/0292156 A1 | 12/2006 | Campbell | |
| 2016/0009805 A1 | 1/2016 | Kowanetz | |
| 2016/0067356 A1 | 3/2016 | Campbell | |

FOREIGN PATENT DOCUMENTS

EP     2161339 A1    3/2010

OTHER PUBLICATIONS

Anikeeva et al., "Integrin receptors on tumor cells facilitate NK cell-mediated antibody-dependent cytotoxicity," Eur. J. Immunol., 2014, vol. 44, pp. 2331-2339.

Binyamin et al., "Blocking NK Cell Inhibitory Self-Recognition Promotes Antibody-Dependent Cellular Cytotoxicity in a Model of Ani-Limphoma Therapy," J Immunol 2008, vol. 180, pp. 6392-6401.

Boissel et al., "NK-92: An "Off the Shelf" Target-Specific Cytotoxic Cell Therapeutic," Cytotherapy, & 21$^{st}$ Annual Meeting of the International-Society-for Cellular-Therapy (ISCT); Las Vegas, NV, USA; May 27, 2015, vol. 17, No. 6, Suppl. S, S19, Jun. 1, 2015, p. 44.

Clëmenceau et al., "In Vitro and In Vivo Comparison of Lymphocytes Transduced with a Human CD16 or with a Chimeric Antigen Receptor Reveals Potential Off-Target Interactions due to the IgG2 CH2-CH3 CAR-Spacer," Journal of Immunology Research, Oct. 22, 2015, vol. 2015, pp. 1-13.

European Application No. 16773863.2, European Search Report dated Oct. 10, 2018, 3 pages.

Nakadate et al., "KRAS mutation confers resistance to antibody-dependent cellular cytotoxicity of cetuximab against human colorectal cancer cells," Int. J. Cancer, 2014, vol. 134, pp. 2146-2155.

Koene, Harry, et al. "FcyRIIIa-158V /F polymorphism influences the binding ofIgG 1-12 by natural killer cell FcyRIIIa-48L/R/H phenotype," Blood, 1997, 90 (3) p. 1109-1114, abstract.

Straathof Karin C. et al. "An inducible caspase 9 safety switch for T-cell therapy," Blood, Jun. 1, 2005, vol. 105, No. 11, p. 4247-4254, especially abstract, p. 4248-4249.

Tam Y.K. et al. "Characterization of genetically altered, interleukin 2-independent natural 8 killer cell lines suitable for adoptive cellular immunotherapy," Human Gene Therapy, 1999, 10(8), p. 1359-1373, especially abstract, p. 1363.

PCT/US2016/024318, "International Search Report and Written Opinion," dated Sep. 21, 2016, 5 pages.

(Continued)

*Primary Examiner* — Brad Duffy
(74) *Attorney, Agent, or Firm* — Kilpatrick Townsend & Stockton, LLP

(57) ABSTRACT

This invention is directed to treatment of a subject having or suspected of having a cancer comprising administering to the subject a monoclonal antibody and NK-92 expressing Fc receptor.

11 Claims, 4 Drawing Sheets

Specification includes a Sequence Listing.

(56) References Cited

OTHER PUBLICATIONS

Konstantinidis, et al., "Targeting IL-2 to the endoplasmic reticulum confines autocrine growth stimulation to NK-92 cells, Experimental Hematology," 2005, 33, p. 159-164.

Stasi, et al., "Inducible Apoptosis as a Safety Switch for Adoptive Cell Therapy, The New England Journal of Medicine," 2011, 365, p. 1673-1683.

Tassev, et al., "Retargeting NK92 cells using an HLA-A2-restricted, EBNA3C-specific chimeric antigen receptor," Cancer Gene Therapy, 2012, 19, p. 84-100.

Dall'Ozzo, et al., "Rituximab-Dependent Cytotoxicity by Natural Killer Cells: Influce of *FCGR3A* Polymorphism on the Concentration-Effect Relationship," Cancer Research, 2004, 64, p. 4664-4669.

\* cited by examiner

SEQUENCE LISTING

<160> NUMBER OF SEQ ID NOS: 7

<210> SEQ ID NO 1
<211> LENGTH: 236
<212> TYPE: PRT
<213> ORGANISM: Homo sapiens

<400> SEQUENCE: 1

Arg Thr Glu Asp Leu Pro Lys Ala Val Val Phe Leu Glu Pro Gln Trp
1               5                   10                  15

Tyr Arg Val Leu Glu Lys Asp Ser Val Thr Leu Lys Cys Gln Gly Ala
            20                  25                  30

Tyr Ser Pro Glu Asp Asn Ser Thr Gln Trp Phe His Asn Glu Ser Leu
        35                  40                  45

Ile Ser Ser Gln Ala Ser Ser Tyr Phe Ile Asp Ala Ala Thr Val Asp
    50                  55                  60

Asp Ser Gly Glu Tyr Arg Cys Gln Thr Asn Leu Ser Thr Leu Ser Asp
65                  70                  75                  80

Pro Val Gln Leu Glu Val His Ile Gly Trp Leu Leu Leu Gln Ala Pro
                85                  90                  95

Arg Trp Val Phe Lys Glu Glu Asp Pro Ile His Leu Arg Cys His Ser
            100                 105                 110

Trp Lys Asn Thr Ala Leu His Lys Val Thr Tyr Leu Gln Asn Gly Lys
        115                 120                 125

Gly Arg Lys Tyr Phe His His Asn Ser Asp Phe Tyr Ile Pro Lys Ala
    130                 135                 140

Thr Leu Lys Asp Ser Gly Ser Tyr Phe Cys Arg Gly Leu Phe Gly Ser
145                 150                 155                 160

```
Lys Asn Val Ser Ser Glu Thr Val Asn Ile Thr Ile Thr Gln Gly Leu
                165                 170                 175

Ala Val Ser Thr Ile Ser Ser Phe Phe Pro Gly Tyr Gln Val Ser
                180                 185                 190

Phe Cys Leu Val Met Val Leu Leu Phe Ala Val Asp Thr Gly Leu Tyr
                195                 200                 205

Phe Ser Val Lys Thr Asn Ile Arg Ser Ser Thr Arg Asp Trp Lys Asp
210                 215                 220

His Lys Phe Lys Trp Arg Lys Asp Pro Gln Asp Lys
225                 230                 235

<210> SEQ ID NO 2
<211> LENGTH: 236
<212> TYPE: PRT
<213> ORGANISM: Homo sapiens

<400> SEQUENCE: 2

Arg Thr Glu Asp Leu Pro Lys Ala Val Val Phe Leu Glu Pro Gln Trp
1               5                   10                  15

Tyr Arg Val Leu Glu Lys Asp Ser Val Thr Leu Lys Cys Gln Gly Ala
                20                  25                  30

Tyr Ser Pro Glu Asp Asn Ser Thr Gln Trp Phe His Asn Glu Ser Leu
            35                  40                  45

Ile Ser Ser Gln Ala Ser Ser Tyr Phe Ile Asp Ala Ala Thr Val Asp
        50                  55                  60

Asp Ser Gly Glu Tyr Arg Cys Gln Thr Asn Leu Ser Thr Leu Ser Asp
65                  70                  75                  80

Pro Val Gln Leu Glu Val His Ile Gly Trp Leu Leu Leu Gln Ala Pro
                85                  90                  95

Arg Trp Val Phe Lys Glu Glu Asp Pro Ile His Leu Arg Cys His Ser
                100                 105                 110

Trp Lys Asn Thr Ala Leu His Lys Val Thr Tyr Leu Gln Asn Gly Lys
                115                 120                 125

Gly Arg Lys Tyr Phe His His Asn Ser Asp Phe Tyr Ile Pro Lys Ala
            130                 135                 140

Thr Leu Lys Asp Ser Gly Ser Tyr Phe Cys Arg Gly Leu Val Gly Ser
145                 150                 155                 160

Lys Asn Val Ser Ser Glu Thr Val Asn Ile Thr Ile Thr Gln Gly Leu
                165                 170                 175

Ala Val Ser Thr Ile Ser Ser Phe Phe Pro Gly Tyr Gln Val Ser
                180                 185                 190

Phe Cys Leu Val Met Val Leu Leu Phe Ala Val Asp Thr Gly Leu Tyr
                195                 200                 205

Phe Ser Val Lys Thr Asn Ile Arg Ser Ser Thr Arg Asp Trp Lys Asp
210                 215                 220

His Lys Phe Lys Trp Arg Lys Asp Pro Gln Asp Lys
225                 230                 235

<210> SEQ ID NO 3
<211> LENGTH: 254
<212> TYPE: PRT
<213> ORGANISM: Homo sapiens
```

-continued

```
<400> SEQUENCE: 3

Met Trp Gln Leu Leu Leu Pro Thr Ala Leu Leu Leu Val Ser Ala
1               5                   10                  15

Gly Met Arg Thr Glu Asp Leu Pro Lys Ala Val Val Phe Leu Glu Pro
            20                  25                  30

Gln Trp Tyr Arg Val Leu Glu Lys Asp Ser Val Thr Leu Lys Cys Gln
            35                  40                  45

Gly Ala Tyr Ser Pro Glu Asp Asn Ser Thr Gln Trp Phe His Asn Glu
50                  55                  60

Ser Leu Ile Ser Ser Gln Ala Ser Ser Tyr Phe Ile Asp Ala Ala Thr
65                  70                  75                  80

Val Asp Asp Ser Gly Glu Tyr Arg Cys Gln Thr Asn Leu Ser Thr Leu
                85                  90                  95

Ser Asp Pro Val Gln Leu Glu Val His Ile Gly Trp Leu Leu Leu Gln
            100                 105                 110

Ala Pro Arg Trp Val Phe Lys Glu Glu Asp Pro Ile His Leu Arg Cys
            115                 120                 125

His Ser Trp Lys Asn Thr Ala Leu His Lys Val Thr Tyr Leu Gln Asn
130                 135                 140

Gly Lys Gly Arg Lys Tyr Phe His His Asn Ser Asp Phe Tyr Ile Pro
145                 150                 155                 160

Lys Ala Thr Leu Lys Asp Ser Gly Ser Tyr Phe Cys Arg Gly Leu Phe
                165                 170                 175

Gly Ser Lys Asn Val Ser Ser Glu Thr Val Asn Ile Thr Ile Thr Gln
            180                 185                 190

Gly Leu Ala Val Ser Thr Ile Ser Ser Phe Phe Pro Pro Gly Tyr Gln
            195                 200                 205

Val Ser Phe Cys Leu Val Met Val Leu Leu Phe Ala Val Asp Thr Gly
210                 215                 220

Leu Tyr Phe Ser Val Lys Thr Asn Ile Arg Ser Ser Thr Arg Asp Trp
225                 230                 235                 240

Lys Asp His Lys Phe Lys Trp Arg Lys Asp Pro Gln Asp Lys
                245                 250

<210> SEQ ID NO 4
<211> LENGTH: 254
<212> TYPE: PRT
<213> ORGANISM: Homo sapiens

<400> SEQUENCE: 4

Met Trp Gln Leu Leu Leu Pro Thr Ala Leu Leu Leu Val Ser Ala
1               5                   10                  15

Gly Met Arg Thr Glu Asp Leu Pro Lys Ala Val Val Phe Leu Glu Pro
            20                  25                  30

Gln Trp Tyr Arg Val Leu Glu Lys Asp Ser Val Thr Leu Lys Cys Gln
            35                  40                  45

Gly Ala Tyr Ser Pro Glu Asp Asn Ser Thr Gln Trp Phe His Asn Glu
50                  55                  60

Ser Leu Ile Ser Ser Gln Ala Ser Ser Tyr Phe Ile Asp Ala Ala Thr
65                  70                  75                  80

Val Asp Asp Ser Gly Glu Tyr Arg Cys Gln Thr Asn Leu Ser Thr Leu
                85                  90                  95

Ser Asp Pro Val Gln Leu Glu Val His Ile Gly Trp Leu Leu Leu Gln
            100                 105                 110
```

Ala Pro Arg Trp Val Phe Lys Glu Glu Asp Pro Ile His Leu Arg Cys
        115                 120                 125

His Ser Trp Lys Asn Thr Ala Leu His Lys Val Thr Tyr Leu Gln Asn
        130                 135                 140

Gly Lys Gly Arg Lys Tyr Phe His His Asn Ser Asp Phe Tyr Ile Pro
145                 150                 155                 160

Lys Ala Thr Leu Lys Asp Ser Gly Ser Tyr Phe Cys Arg Gly Leu Val
                165                 170                 175

Gly Ser Lys Asn Val Ser Ser Glu Thr Val Asn Ile Thr Ile Thr Gln
                180                 185                 190

Gly Leu Ala Val Ser Thr Ile Ser Ser Phe Phe Pro Pro Gly Tyr Gln
        195                 200                 205

Val Ser Phe Cys Leu Val Met Val Leu Leu Phe Ala Val Asp Thr Gly
        210                 215                 220

Leu Tyr Phe Ser Val Lys Thr Asn Ile Arg Ser Ser Thr Arg Asp Trp
225                 230                 235                 240

Lys Asp His Lys Phe Lys Trp Arg Lys Asp Pro Gln Asp Lys
                245                 250

<210> SEQ ID NO 5
<211> LENGTH: 765
<212> TYPE: DNA
<213> ORGANISM: Homo sapiens

<400> SEQUENCE: 5
atgtggcagc tgctcctccc aactgctctg ctacttctag tttcagctgg catgcggact    60
gaagatctcc caaggctgt ggtgttcctg gagcctcaat ggtacagggt gctcgagaag   120
gacagtgtga ctctgaagtg ccagggagcc tactcccctg aggacaattc cacacagtgg   180
tttcacaatg agagcctcat ctcaagccag gcctcgagct acttcattga cgctgccaca   240
gtcgacgaca gtggagagta caggtgccag acaaacctct ccaccctcag tgacccggtg   300
cagctagaag tccatatcgg ctggctgttg ctccaggccc ctcggtgggt gttcaaggag   360
gaagacccta ttcacctgag gtgtcacagc tggaagaaca ctgctctgca taaggtcaca   420
tatttacaga atggcaaagg caggaagtat tttcatcata attctgactt ctacattcca   480
aaagccacac tcaaagacag cggctcctac ttctgcaggg ggcttttggg gagtaaaaat   540
gtgtcttcag agactgtgaa catcaccatc actcaaggtt tggcagtgtc aaccatctca   600
tcattctttc cacctgggta ccaagtctct ttctgcttgg tgatggtact ccttttttgca   660 gtggacacag actatatttt ctctgtgaag acaaacattc gaagctcaac aagagactgg   720
aaggaccata aatttaaatg gagaaaggac cctcaagaca aatga                  765

<210> SEQ ID NO 6
<211> LENGTH: 153
<212> TYPE: PRT
<213> ORGANISM: Homo sapiens

<400> SEQUENCE: 6

Met Tyr Arg Met Gln Leu Leu Ser Cys Ile Ala Leu Ser Leu Ala Leu
1               5                   10                  15

Val Thr Asn Ser Ala Pro Thr Ser Ser Ser Thr Lys Lys Thr Gln Leu
                20                  25                  30

Gln Leu Glu His Leu Leu Leu Asp Leu Gln Met Ile Leu Asn Gly Ile
        35                  40                  45

```
Asn Asn Tyr Lys Asn Pro Lys Leu Thr Arg Met Leu Thr Phe Lys Phe
    50              55                  60

Tyr Met Pro Lys Lys Ala Thr Glu Leu Lys His Leu Gln Cys Leu Glu
65              70                  75                  80

Glu Glu Leu Lys Pro Leu Glu Glu Val Leu Asn Leu Ala Gln Ser Lys
                85                  90                  95

Asn Phe His Leu Arg Pro Arg Asp Leu Ile Ser Asn Ile Asn Val Ile
            100                 105                 110

Val Leu Glu Leu Lys Gly Ser Glu Thr Thr Phe Met Cys Glu Tyr Ala
        115                 120                 125

Asp Glu Thr Ala Thr Ile Val Glu Phe Leu Asn Arg Trp Ile Thr Phe
        130                 135                 140

Cys Gln Ser Ile Ile Ser Thr Leu Thr
145                 150

<210> SEQ ID NO 7
<211> LENGTH: 160
<212> TYPE: PRT
<213> ORGANISM: Homo sapiens

<400> SEQUENCE: 7

Met Tyr Arg Met Gln Leu Leu Ser Cys Ile Ala Leu Ser Leu Ala Leu
1               5                   10                  15

Val Thr Asn Ser Ala Pro Thr Ser Ser Ser Thr Lys Lys Thr Gln Leu
            20                  25                  30

Gln Leu Glu His Leu Leu Leu Asp Leu Gln Met Ile Leu Asn Gly Ile
        35                  40                  45

Asn Asn Tyr Lys Asn Pro Lys Leu Thr Arg Met Leu Thr Phe Lys Phe
    50              55                  60

Tyr Met Pro Lys Lys Ala Thr Glu Leu Lys His Leu Gln Cys Leu Glu
65              70                  75                  80

Glu Glu Leu Lys Pro Leu Glu Glu Val Leu Asn Leu Ala Gln Ser Lys
                85                  90                  95

Asn Phe His Leu Arg Pro Arg Asp Leu Ile Ser Asn Ile Asn Val Ile
            100                 105                 110

Val Leu Glu Leu Lys Gly Ser Glu Thr Thr Phe Met Cys Glu Tyr Ala
        115                 120                 125

Asp Glu Thr Ala Thr Ile Val Glu Phe Leu Asn Arg Trp Ile Thr Phe
        130                 135                 140

Cys Gln Ser Ile Ile Ser Thr Leu Thr Gly Ser Glu Lys Asp Glu Leu
145                 150                 155                 160
```

GENETICALLY MODIFIED NK-92 CELLS AND MONOCLONAL ANTIBODIES FOR THE TREATMENT OF CANCER

CROSS-REFERENCE TO RELATED APPLICATIONS

This application is a continuation of U.S. application Ser. No. 16/903,882, filed Jun. 17, 2020, which is a continuation of U.S. application Ser. No. 16/541,847, filed Aug. 15, 2019, issued Aug. 11, 2020 as U.S. Pat. No. 10,736,921; which is a continuation of U.S. application Ser. No. 15/529,848, filed May 25, 2017, issued Oct. 29, 2019 as U.S. Pat. No. 10,456,420; which is a national stage under 35 U.S.C. § 371 of application no. PCT/US2016/024318, filed Mar. 25, 2016; which claims priority benefit of U.S. provisional application No. 62/139,258, filed Mar. 27, 2015. Each application is incorporated by reference herein.

REFERENCE TO SUBMISSION OF A SEQUENCE LISTING AS A TEXT FILE

The Sequence Listing written in file 099083_1242558_SEQ_LST_03_30_2021.txt created on Mar. 30, 2021, 13,059 bytes, machine format IBM-PC, MS-Windows operating system, is hereby incorporated by reference in its entirety for all purposes.

BACKGROUND OF THE INVENTION

Anticancer treatment with monoclonal antibodies (mAbs) has significantly improved the clinical outcome in patients with cancer, especially when combined with chemotherapy. However, often the patients ultimately relapse. Natural killer cells could also be used as cytotoxic effector cells for cell-based immunotherapy.

NK-92 is a cytolytic cancer cell line which was discovered in the blood of a subject suffering from a non-Hodgkins lymphoma and then immortalized ex vivo. NK-92 cells are derived from NK cells, but lack the major inhibitory receptors that are displayed by normal NK cells, while retaining the majority of the activating receptors. NK-92 cells do not, however, attack normal cells nor do they elicit an unacceptable immune rejection response in humans. Characterization of the NK-92 cell line is disclosed in WO 1998/49268 and U.S. Patent Application Publication No. 2002-0068044. NK-92 cells have also been evaluated as a potential therapeutic agent in the treatment of certain cancers.

Although NK-92 cells retain almost all of the activating receptors and cytolytic pathways associated with NK cells, they do not express CD16 on their cell surfaces. CD16 is an Fc receptor which recognizes and binds to the Fc portion of an antibody to activate NK cells for antibody-dependent cellular cytotoxicity (ADCC). Due to the absence of CD16 receptors, NK-92 cells are unable to lyse target cells via the ADCC mechanism.

The present invention provides a solution to the aforementioned problems, by augmenting the cytotoxic effect of some molecular antibodies by simultaneously or consequently administering to a subject in need of anticancer treatment NK-92 cells that express Fc receptors.

BRIEF SUMMARY OF ASPECTS OF THE INVENTION

In one aspect, the invention comprises co-administering to a subject in need of anticancer treatment a monoclonal antibody having cytotoxic effects on the target cancer cells and NK-92 cells engineered express an Fc receptor. This combination synergizes the anti-cancer effects of NK cells with the anticancer effects of therapeutic antibodies.

Thus, in one embodiment, the invention provides a method for treating cancer in a subject in need thereof comprising administering to the subject a monoclonal antibody having a cytotoxic effect on the target cancer cell and FcR-expressing NK-92 cells. In some embodiments, the FcR is CD16. In one aspect of the invention, the NK-92 cells are genetically modified to express an Fc receptor encoding a polypeptide having at least 90% sequence identity with SEQ ID NO:1 (FCγRIII-A or CD16 having a phenylalanine at position 158 (F-158); or at least 90% identity to SEQ ID NO:2 (CD16 having a valine at position 158 (F158V), higher affinity form). In typical embodiments, the CD16 polypeptide has a valine at position 158.

In further embodiments, the NK-92 cells are additionally modified to express a cytokine, such as IL-2. In some embodiments, the cytokine is targeted to the endoplasmic reticulum. In specific embodiments, the cytokine is interleukin-2 or a variant thereof, that is targeted to the endoplasmic reticulum. In some embodiments, the NK-92 cells are modified to express a polypeptide having a sequence of SEQ ID NO:7.

In other embodiments, the NK-92 cells are further modified to express a suicide gene. In one aspect, the suicide gene is inducible caspase 9.

The compositions of the invention are useful for the treatment of cancer, including, but not limited to, cancers such as multiple myeloma, leukemias, lymphomas, metastatic breast cancer or gastric carcinoma.

The monoclonal antibody that is administered to the patient can be a naked monoclonal antibody, a conjugated monoclonal antibody, or a bispecific monoclonal antibody. In some embodiments, the monoclonal antibody is alemtuzumab, rituxumab, trastuzumab, ibritumomab, gemtuzumab, brentuximab, adotranstuzumab, blinatumomab, daratumumab or elotuzumab.

In some embodiments, the monoclonal antibody and the FcR-expressing NK-92 cells are administered simultaneously to the subject. In other embodiments, the subject is administered the monoclonal antibody and subsequently administered the FcR-expressing NK-92 cells, e.g., within 24 hours; or within 24 to 72 hours, after administration of the monoclonal antibody.

In some aspects, the invention relates to use of an NK-92 cells genetically modified to express an FcR, such as CD16, with a cytotoxic monoclonal antibody of the treatment of cancer. Thus, in some embodiments the invention provides use of NK-92 cells that are genetically modified to express CD16 with a cytotoxic monoclonal antibody for a patient that has cancer. In some embodiments, the Fc receptor is a CD16 having a valine at position 158 of the mature form of CD16. In some embodiments, the Fc receptor comprises a polynucleotide sequence encoding a polypeptide having at least 90% sequence identity with SEQ ID NO:1 or SEQ ID NO:2, or the polynucleotide encodes SEQ ID NO:1 or SEQ ID NO:2. In some embodiments, the FcR-expressing NK-92 cells are genetically modified to express a cytokine such as interleukin-2 or a variant thereof. In some embodiments, the interleukin-2 is targeted to the endoplasmic reticulum. In some embodiments, the FcR-expressing NK-92 cells are modified to express an interleukin-2 sequence as set forth in SEQ ID NO:7. In some embodiments, the Fc receptor and at least one cytokine are encoded by different vectors. Alternatively, the Fc receptor and at least one cytokine are encoded by the same vector. In some embodiments, the Fc receptor comprises a CD16 polypeptide having a V at position 158 and the NK-92 cells are further genetically modified to express human interleukin-2, wherein the interleukin 2 is targeted to the endoplasmic reticulum. The FcR-expressing NK-92 cells may also be further modified to express a suicide gene, such as inducible caspase 9. In some embodiments, the cancer is leukemia, non-Hodgkin's lymphoma, metastatic breast cancer or gastric carcinoma. The monoclonal antibody may be a naked monoclonal antibody, a conjugated monoclonal antibody, or a bispecific monoclonal antibody. In some embodiments, the monoclonal antibody is alemtuzumab, rituximab, trastuzumab, ibritumomab, brentuximab, gemtuzumab, adotranstuzumab, blinatumomab, avelumab, daratumumab or elotuzumab. In some embodiments, the monoclonal antibody and the FcR-expressing NK-92 cells are administered simultaneously to the subject. In some embodiments, the subject is administered the monoclonal antibody and subsequently treated with the genetically modified FcR-expressing NK-92 cells. In some embodiments, the monoclonal antibody is injected intravenously into the subject. In other embodiments, the genetically modified FcR-expressing NK-92 cells are injected into the bone marrow.

The foregoing general description and the following detailed description are exemplary and explanatory and are intended to provide further explanation of the invention as claimed. Other objects, advantages and novel features will be readily apparent to those skilled in the art from the following detailed description of the invention.

BRIEF DESCRIPTION OF THE DRAWINGS

The objects, features and advantages of the present invention will be more readily appreciated upon reference to the following disclosure when considered in conjunction with the accompanying drawings.

DETAILED DESCRIPTION OF THE INVENTION

Figure 1:
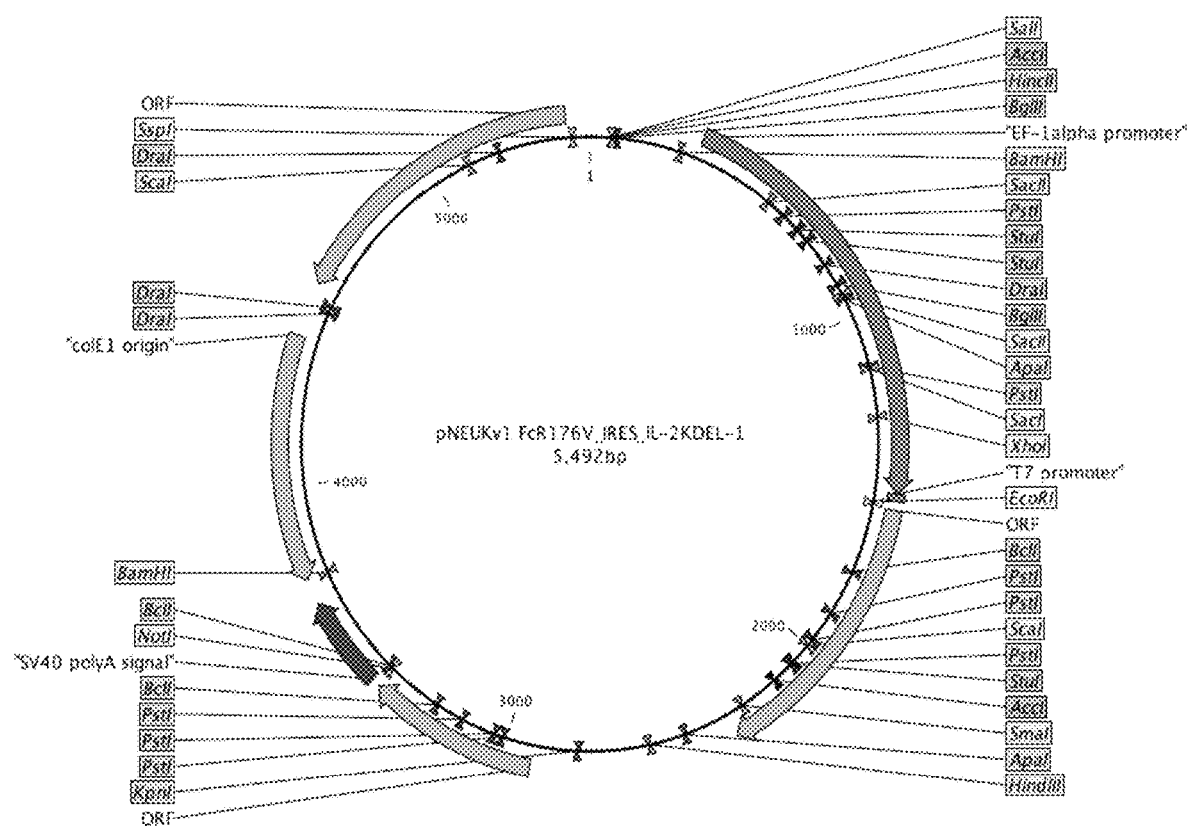
FIG. 1 shows a schematic representation of a plasmid expressing a modified form of IL-2 with ERRS (endoplasmic reticulum retention signal) and CD16.

In one aspect, the disclosure relates to the use of NK-92 cells modified to express FcR and monoclonal antibodies for the treatment of cancer in a subject in need thereof. Malignant cells are able to develop mechanisms to escape the immunological protection that innate immune cells, such as dendritic cells and natural killer cells, and adaptive immune cells, such as T cells and B cells, provide. There is therefore an urgent need for reducing incidence of tumor relapse in subjects having cancer or suspected of having cancer.

NK-92 cells present the attractive feature that they can easily be propagated and expanded in vitro. However, they do not express the IgG Fc receptor FcγRIII, and thus these cells are unable to act via antibody-dependent cell-mediated cytotoxicity (ADCC). The present invention is based on the predicament that genetic transformation of the NK-92 cells to express the IgG Fc receptor FcγRIII would enhance NK-tumor cell interaction and allow the NK cells to work in unison with monoclonal antibodies that kill target cells through ADCC. Thus, the separate cytotoxic effect of NK-92 cells and monoclonal antibodies may be augmented when the monoclonal antibodies and the NK-92 cells are administered simultaneously or in close temporal relation to a subject that has cancer or is otherwise in need of cancer treatment.

Accordingly, the present invention provides for the use of NK-92 cells that are genetically modified to express the high affinity form of the transmembrane immunoglobulin γ Fc region receptor III-A (FcγRIII-A or CD16 in which a valine is present at position 158 of the mature form of the polypeptide).

In some embodiments the FcR-expressing NK-92 cells may be further modified to express IL-2. In such cells, the expression of IL-2 in the cells is typically directed to the endoplasmic reticulum. This feature prevents undesirable effects of systemic administration of IL-2, such as toxicity affecting the cardiovascular, gastrointestinal, respiratory and nervous systems. In some embodiments, when the FcR-expressing NK-92 cells are further modified to express IL-2, a suicide gene may also be inserted into these cells to prevent unregulated endogenous expression of IL-2, that could lead to the potential development of mutants with autonomous growth. In some embodiments, the suicide gene is inducible caspase 9.

The FcR-expressing NK-92 cells produced according to the invention are administered in conjunction with a monoclonal antibody targeting cancerous cells to a subject having or suspected of having cancer for effective treatment of cancerous diseases.

Administration of the FcR-expressing NK-92 cells may be carried out simultaneously with the administration of the monoclonal antibody, or in a sequential manner. In some embodiments, the FcR-expressing NK-92 cells are administered to the subject within 24 hours after the subject has been treated with the monoclonal antibody.

Terminology

Unless defined otherwise, all technical and scientific terms used herein have the same meaning as commonly understood by one of ordinary skill in the art to which this invention belongs.

In this specification and in the claims that follow, reference will be made to a number of terms that shall be defined to have the following meanings:

The terminology used herein is for the purpose of describing particular embodiments only and is not intended to be limiting of the invention. As used herein, the singular forms "a", "an" and "the" are intended to include the plural forms as well, unless the context clearly indicates otherwise.

All numerical designations, e.g., pH, temperature, time, concentration, amounts, an molecular weight, including ranges, are approximations which are varied (+) or (−) by increments of 0.1 or 1.0, where appropriate. It is to be understood, although not always explicitly stated, that all numerical designations may be preceded by the term "about." It is also to be understood, although not always explicitly stated, that the reagents described herein are merely exemplary and that equivalents of such are known in the art.

"Optional" or "optionally" means that the subsequently described event or circumstance can or cannot occur, and that the description includes instances where the event or circumstance occurs and instances where it does not.

The term "comprising" is intended to mean that the compositions and methods include the recited elements, but do not exclude others. "Consisting essentially of" when used to define compositions and methods, refers to the specified materials or steps and those that do not materially affect the basic and novel characteristic(s) of the claimed invention.

"Consisting of" shall mean excluding more than trace amounts of other ingredients and substantial method steps recited. Embodiments defined by each of these transition terms are within the scope of this invention.

As used to describe the present invention, "immunotherapy" refers to the use of NK-92 cells, modified or unmodified, in combination with antibody, naturally occurring or modified NK cell or T-cell, whether alone or in combination, and which are capable of inducing cytotoxicity when contacting a target cell.

As used to describe the present invention, "natural killer (NK) cells" are cells of the immune system that kill target cells in the absence of a specific antigenic stimulus, and without restriction according to MHC class. Target cells may be tumor cells or cells harboring viruses. NK cells are characterized by the presence of CD56 and the absence of CD3 surface markers.

The term "endogenous NK cells" is used to refer to NK cells derived from a donor (or the patient), as distinguished from the NK-92 cell line. Endogenous NK cells are generally heterogeneous populations of cells within which NK cells have been enriched. Endogenous NK cells may be intended for autologous or allogeneic treatment of a patient.

"NK-92 cells" refer to the immortal NK cell line, NK-92, which was originally obtained from a patient having non-Hodgkin's lymphoma. For purposes of this invention and unless indicated otherwise, the term "NK-92" is intended to refer to the original NK-92 cell lines as well as NK-92 cell lines that have been modified (e.g., by introduction of exogenous genes). NK-92 cells and exemplary and non-limiting modifications thereof are described in U.S. Pat. Nos. 7,618,817; 8,034,332; and 8,313,943, all of which are incorporated herein by reference in their entireties.

"Modified NK-92 cell" refers to an NK-92 cell that further comprises a vector that encodes for transgenes, including CD16. In some embodiments, the modified FcR-expressing NK-92 cells may be further modified to express a cytokine such as IL-2, and/or suicide genes.

As used herein, "non-irradiated NK-92 cells" are NK-92 cells that have not been irradiated. Irradiation renders the cells incapable of growth and proliferation. In some embodiments, it is envisioned that the NK-92 cells for administration will be irradiated at a treatment facility or some other point prior to treatment of a patient, since the time between irradiation and infusion should be no longer than four hours in order to preserve optimal activity. Alternatively, NK-92 cells may be inactivated by another mechanism.

As used to describe the present invention, "inactivation" of the NK-92 cells renders them incapable of growth. Inactivation may also relate to the death of the NK-92 cells. It is envisioned that the NK-92 cells may be inactivated after they have effectively purged an ex vivo sample of cells related to a pathology in a therapeutic application, or after they have resided within the body of a mammal a sufficient period of time to effectively kill many or all target cells residing within the body. Inactivation may be induced, by way of non-limiting example, by administering an inactivating agent to which the NK-92 cells are sensitive.

As used to describe the present invention, the terms "cytotoxic" and "cytolytic", when used to describe the activity of effector cells such as NK cells, are intended to be synonymous. In general, cytotoxic activity relates to killing of target cells by any of a variety of biological, biochemical, or biophysical mechanisms. Cytolysis refers more specifically to activity in which the effector lyses the plasma membrane of the target cell, thereby destroying its physical integrity. This results in the killing of the target cell. Without wishing to be bound by theory, it is believed that the cytotoxic effect of NK cells is due to cytolysis.

The term "kill" with respect to a cell/cell population is directed to include any type of manipulation that will lead to the death of that cell/cell population.

The term "Fc receptor" refers to a protein found on the surface of certain cells (e.g., natural killer cells) that contribute to the protective functions of the immune cells by binding to part of an antibody known as the Fc region. Binding of the Fc region of an antibody to the Fc receptor (FcR) of a cell stimulates phagocytic or cytotoxic activity of a cell via antibody-mediated phagocytosis or antibody-dependent cell-mediated cytotoxicity (ADCC). FcRs are classified based on the type of antibody they recognize. For example, Fc-gamma receptors (FCγR) bind to the IgG class of antibodies. FCγRIII-A (also called CD16) is a low affinity Fc receptor bind to IgG antibodies and activate ADCC. FCγRIII-A are typically found on NK cells. A representative polynucleotide sequence encoding a native form of CD16 is shown in SEQ ID NO:5.

The terms "polynucleotide", "nucleic acid" and "oligonucleotide" are used interchangeably and refer to a polymeric form of nucleotides of any length, either deoxyribonucleotides or ribonucleotides or analogs thereof. Polynucleotides can have any three dimensional structure and may perform any function, known or unknown. The following are non-limiting examples of polynucleotides: a gene or gene fragment (for example, a probe, primer, EST or SAGE tag), exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes and primers. A polynucleotide can comprise modified nucleotides, such as methylated nucleotides and nucleotide analogs. If present, modifications to the nucleotide structure can be imparted before or after assembly of the polynucleotide. The sequence of nucleotides can be interrupted by non-nucleotide components. A polynucleotide can be further modified after polymerization, such as by conjugation with a labeling component. The term also refers to both double and single stranded molecules. Unless otherwise specified or required, any embodiment of this invention that is a polynucleotide encompasses both the double stranded form and each of two complementary single stranded forms known or predicted to make up the double stranded form.

A polynucleotide is composed of a specific sequence of four nucleotide bases: adenine (A); cytosine (C); guanine (G); thymine (T); and uracil (U) for thymine when the polynucleotide is RNA. Thus, the term "polynucleotide sequence" is the alphabetical representation of a polynucleotide molecule.

As used herein, "percent identity" refers to sequence identity between two peptides or between two nucleic acid molecules. Percent identity can be determined by comparing a position in each sequence which may be aligned for purposes of comparison. When a position in the compared sequence is occupied by the same base or amino acid, then the molecules are identical at that position. As used herein, the phrase "homologous" or "variant" nucleotide sequence," or "homologous" or "variant" amino acid sequence refers to sequences characterized by identity, at the nucleotide level or amino acid level, of at least a specified percentage. Homologous nucleotide sequences include those sequences coding for naturally occurring allelic variants and mutations of the nucleotide sequences set forth herein. Homologous nucleotide sequences include nucleotide sequences encoding for a protein of a mammalian species other than humans. Homologous amino acid sequences include those amino acid sequences which contain conservative amino acid substitutions and which polypeptides have the same binding and/or activity. In some embodiments, a homologous nucleotide or amino acid sequence has at least 60% or greater, for example at least 70%, or at least 80%, at least 85% or greater, with a comparator sequence. In some embodiments, a homologous nucleotide or amino acid sequence has at least 90%, 91%, 92%, 93%, 94%, 95%, 96%, 97%, 98% or 99% identity with a comparator sequence. In some embodiments, a homologous amino acid sequence has no more than 15, nor more than 10, nor more than 5 or no more than 3 conservative amino acid substitutions. Percent identity can be determined by, for example, the Gap program (Wisconsin Sequence Analysis Package, Version 8 for UNIX, Genetics Computer Group, University Research Park, Madison Wis.), using default settings, which uses the algorithm of Smith and Waterman (Adv. Appl. Math., 1981, 2, 482-489).

The term "express" refers to the production of a gene product. The term "transient" when referred to expression means a polynucleotide is not incorporated into the genome of the cell.

The term "cytokine" or "cytokines" refers to the general class of biological molecules which effect cells of the immune system. Exemplary cytokines for use in practicing the invention include but are not limited to interferons and interleukins (IL), in particular IL-2, IL-12, IL-15, IL-18 and IL-21. In preferred embodiments, the cytokine is IL-2.

As used herein, the term "vector" refers to a non-chromosomal nucleic acid comprising an intact replicon such that the vector may be replicated when placed within a permissive cell, for example by a process of transformation. A vector may replicate in one cell type, such as bacteria, but have limited ability to replicate in another cell, such as mammalian cells. Vectors may be viral or non-viral. Exemplary non-viral vectors for delivering nucleic acid include naked DNA; DNA complexed with cationic lipids, alone or in combination with cationic polymers; anionic and cationic liposomes; DNA-protein complexes and particles comprising DNA condensed with cationic polymers such as heterogeneous polylysine, defined-length oligopeptides, and polyethylene imine, in some cases contained in liposomes; and the use of ternary complexes comprising a virus and polylysine-DNA.

As used herein, the term "targeted" is intended to include, but is not limited to, directing proteins or polypeptides to appropriate destinations in the cell or outside of it. The targeting is typically achieved through signal peptides or targeting peptides, which are a stretch of amino acid residues in a polypeptide chain. These signal peptides can be located anywhere within a polypeptide sequence, but are often located on the N-terminus. Polypeptides can also be engineered to have a signal peptide on the C-terminus. Signal peptides can direct a polypeptide for extracellular section, location to plasma membrane, golgi, endosomes, endoplasmic reticulum, and other cellular compartments. For example, polypeptides with a particular amino acid sequence on their C-terminus (e.g., KDEL) are retained in the ER lumen or transported back the ER lumen.

The term "suicide gene" is one that allows for the negative selection of the cells. A suicide gene is used as a safety system, allowing the cells expressing the gene to be killed by introduction of a selective agent. This is desirable in case the recombinant gene causes a mutation leading to uncontrolled cell growth. A number of suicide gene systems have been identified, including the herpes simplex virus thymidine kinase (TK) gene, the cytosine deaminase gene, the varicella-zoster virus thymidine kinase gene, the nitroreductase gene, the *Escherichia coli* gpt gene, and the *E. coli* Deo gene (also see, for example, Yazawa K, Fisher W E, Brunicardi F C: Current progress in suicide gene therapy for cancer. World J. Surg. 2002 July; 26(7):783-9). In one embodiment, the suicide gene is inducible caspase 9 (iCas9) (Di Stasi, (2011) "Inducible apoptosis as a safety switch for adoptive cell therapy." N Engl J Med 365: 1673-1683. See also Morgan, "Live and Let Die: A New Suicide Gene Therapy Moves to the Clinic" *Molecular Therapy* (2012); 20: 11-13). The TK gene may be a wild-type or mutant TK gene (e.g., tk30, tk75, sr39tk). Cells expressing the TK protein can be killed using ganciclovir.

The term "monoclonal antibody" as used herein, refers to a pure, target-specific antibody produced from a single clone of cells grown in culture and that is capable of proliferating indefinitely. Monoclonal antibodies that may be used according to the invention include naked antibodies, that attach to and block antigens on cancerous cells. In one embodiment, the naked monoclonal antibody is alemtuzumab, which binds to the CD52 antigen in lymphocytes. Also included in the monoclonal antibodies that may be used according to the invention are conjugated monoclonal antibodies, such as tagged, labeled or loaded antibodies. Specifically, the antibodies may be tagged or loaded with a drug or a toxin, or radioactively labeled. Examples of such antibodies include, but are not limited to, ibritumomab, which targets the CD20 antigen; brentuximab, which targets the CD30 antigen, and trastuzumab, which targets the HER2 protein. Other monoclonal antibodies that may be used according to the invention are bispecific monoclonal antibodies, such as blinatumomab, which targets CD19 in lymphoma cells, and CD3 in T cells.

The terms "patient," "subject," "individual," and the like are used interchangeably herein, and refer to any animal, or cells thereof whether in vitro or in situ, amenable to the methods described herein. In certain non-limiting embodiments, the patient, subject or individual is a human.

The term "treating" or "treatment" covers the treatment of a disease or disorder described herein, in a subject, such as a human, and includes: (i) inhibiting a disease or disorder, i.e., arresting its development; (ii) relieving a disease or disorder, i.e., causing regression of the disorder; (iii) slowing progression of the disorder; and/or (iv) inhibiting, relieving, or slowing progression of one or more symptoms of the disease or disorder. The term "administering" or "administration" of a monoclonal antibody or a natural killer cell to a subject includes any route of introducing or delivering the antibody or cells to perform the intended function. Administration can be carried out by any route suitable for the delivery of the cells or monoclonal antibody. Thus, delivery routes can include intravenous, intramuscular, intraperitoneal, or subcutaneous deliver. In some embodiments a monoclonal antibody and/or NK-92 cells are administered directly to the tumor, e.g., by injection into the tumor. Administration includes self-administration and the administration by another.

NK-92 Cells

The NK-92 cell line is a unique cell line that was discovered to proliferate in the presence of interleukin 2 (IL-2). Gong et al., Leukemia 8:652-658 (1994). These cells have high cytolytic activity against a variety of cancers. The NK-92 cell line is a homogeneous cancerous NK cell population having broad anti-tumor cytotoxicity with predictable yield after expansion. Phase I clinical trials have confirmed its safety profile.

The NK-92 cell line is found to exhibit the $CD56^{bright}$, CD2, CD7, CD11a, CD28, CD45, and CD54 surface markers. It furthermore does not display the CD1, CD3, CD4, CD5, CD8, CD10, CD14, CD16, CD19, CD20, CD23, and CD34 markers. Growth of NK-92 cells in culture is dependent upon the presence of recombinant interleukin 2 (rIL-2), with a dose as low as 1 IU/mL being sufficient to maintain proliferation. IL-7 and IL-12 do not support long-term growth, nor do other cytokines tested, including IL-1α, IL-6, tumor necrosis factor α, interferon α, and interferon γ. NK-92 has high cytotoxicity even at a low effector:target (E:T) ratio of 1:1. Gong, et al., supra. NK-92 cells are deposited with the American Type Culture Collection (ATCC), designation CRL-2407.

Heretofore, studies on endogenous NK cells have indicated that IL-2 (1000 IU/mL) is critical for NK cell activation during shipment, but that the cells need not be maintained at 37° C. and 5% carbon dioxide. Koepsell, et al., *Transfusion* 53:398-403 (2013).

Suicide Gene

The term "suicide gene" is one that allows for the negative selection of the cells. A suicide gene is used as a safety system, allowing the cells expressing the gene to be killed by introduction of a selective agent. This is desirable in case the recombinant gene causes a mutation leading to uncontrolled cell growth. A number of suicide gene systems have been identified, including the herpes simplex virus thymidine kinase (TK) gene, the cytosine deaminase gene, the varicella-zoster virus thymidine kinase gene, the nitroreductase gene, the *Escherichia coli* gpt gene, and the *E. coli* Deo gene (also see, for example, Yazawa K, Fisher W E, Brunicardi F C: Current progress in suicide gene therapy for cancer. World J. Surg. 2002 July; 26(7):783-9). As used herein, the suicide gene is active in NK-92 cells. Typically, the suicide gene encodes for a protein that has no ill-effect on the cell but, in the presence of a specific compound, will kill the cell. Thus, the suicide gene is typically part of a system.

In one embodiment, the suicide gene is the thymidine kinase (TK) gene. The TK gene may be a wild-type or mutant TK gene (e.g., tk30, tk75, sr39tk). Cells expressing the TK protein can be killed using ganciclovir.

In another embodiment, the suicide gene is Cytosine deaminase which is toxic to cells in the presence of 5-fluorocytosine. Garcia-Sanchez et al. "Cytosine deaminase adenoviral vector and 5-fluorocytosine selectively reduce breast cancer cells 1 million-fold when they contaminate hematopoietic cells: a potential purging method for autologous transplantation." *Blood* 1998 Jul. 15; 92(2):672-82.

In another embodiment, the suicide gene is cytochrome P450 which is toxic in the presence of ifosfamide or cyclophosphamide. See e.g. Touati et al. "A suicide gene therapy combining the improvement of cyclophosphamide tumor cytotoxicity and the development of an anti-tumor immune response." *Curr Gene Ther.* 2014; 14(3):236-46.

In another embodiment, the suicide gene is iCas9. Di Stasi, (2011) "Inducible apoptosis as a safety switch for adoptive cell therapy." N Engl J Med 365: 1673-1683. See also Morgan, "Live and Let Die: A New Suicide Gene Therapy Moves to the Clinic" *Molecular Therapy* (2012); 20: 11-13. The iCas9 protein induces apoptosis in the presence of a small molecule AP1903. AP1903 is biologically inert small molecule, that has been shown in clinical studies to be well tolerated, and has been used in the context of adoptive cell therapy.

Fc Receptors

Fc receptors bind to the Fc portion of antibodies. Several Fc receptors are known, and differ according to their preferred ligand, affinity, expression, and effect following binding to the antibody.

TABLE 1

Illustrative Fc receptors

| Receptor name | Principal antibody ligand | Affinity for ligand | Cell distribution | Effect following binding to antibody |
|---|---|---|---|---|
| FcγRI (CD64) | IgG1 and IgG3 | High (Kd~ $10^{-9}$ M) | Macrophages Neutrophils Eosinophils Dendritic cells | Phagocytosis Cell activation Activation of respiratory burst Induction of microbe killing |
| FcγRIIA (CD32) | IgG | Low (Kd > $10^{-7}$ M) | Macrophages Neutrophils Eosinophils Platelets Langerhans cells | Phagocytosis Degranulation (eosinophils) |
| FcγRIIB1 (CD32) | IgG | Low (Kd > $10^{-7}$ M) | B Cells Mast cells | No phagocytosis Inhibition of cell activity |
| FcγRIIB2 (CD32) | IgG | Low (Kd > $10^{-7}$ M) | Macrophages Neutrophils Eosinophils | Phagocytosis Inhibition of cell activity |
| FcγRIIIA (CD16a) | IgG | Low (Kd > $10^{-6}$ M) | NK cells Macrophages (certain tissues) | Induction of antibody-dependent cell-mediated cytotoxicity (ADCC) Induction of cytokine release by macrophages |

TABLE 1-continued

Illustrative Fc receptors

| Receptor name | Principal antibody ligand | Affinity for ligand | Cell distribution | Effect following binding to antibody |
| --- | --- | --- | --- | --- |
| FcγRIIIB (CD16b) | IgG | Low (Kd > $10^{-6}$ M) | Eosinophils Macrophages Neutrophils Mast cells Follicular dendritic cells | Induction of microbe killing |
| FcεRI | IgE | High (Kd~ $10^{-10}$ M) | Mast cells Eosinophils Basophils Langerhans cells Monocytes | Degranulation Phagocytosis |
| FcεRII (CD23) | IgE | Low (Kd > $10^{-7}$ M) | B cells Eosinophils Langerhans cells | Possible adhesion molecule IgE transport across human intestinal epithelium Positive-feedback mechanism to enhance allergic sensitization (B cells) |
| FcαRI (CD89) | IgA | Low (Kd > $10^{-6}$ M) | Monocytes Macrophages Neutrophils Eosinophils | Phagocytosis Induction of microbe killing |
| Fcα/μR | IgA and IgM | High for IgM Mid for IgA | B cells Mesangial cells Macrophages | Endocytosis Induction of microbe killing |
| FcRn | IgG | | Monocytes Macrophages Dendritic cells Epithelial cells Endothelial cells Hepatocytes | Transfers IgG from a mother to fetus through the placenta Transfers IgG from a mother to infant in milk Protects IgG from degradation |

In some embodiments NK-92 cells are modified to express an Fc receptor protein on the cell surface.

In some embodiments, the Fc receptor is CD16. For purposes of this disclosure, specific amino acid residues of CD16 are designated with reference to SEQ ID NO:2, or to SEQ ID NO:1, which differs at one position relative to SEQ ID NO:2. Thus, an amino acid residue "at position 158" of a CD16 polypeptide in accordance with the invention is the amino acid residue that corresponds to position 158 of SEQ ID NO:2 (or SEQ ID NO:1), when the CD16 polypeptide and SEQ ID NO:2 are maximally aligned. In some embodiments, NK-92 cells are modified to express a human CD16 that has a phenylalanine at position 158 of the mature form of the protein, e.g., SEQ ID NO:1. In typical embodiments, NK-92 cells are modified to express a high affinity form of human CD16 having a valine at position 158 of the mature form of the protein, e.g., SEQ ID NO:2. Position 158 of the mature protein corresponds to position 176 of the CD16 sequence that includes the native signal peptide. In some embodiments, a CD16 polypeptide is encoded by a polynucleotide that encodes the precursor (i.e., has a native signal peptide) polypeptide sequence of SEQ ID NO:3 or of SEQ ID NO:4.

In some embodiments, a polynucleotide encoding a CD16 polypeptide has at least about 70% polynucleotide sequence identity with a polynucleotide sequence encoding a full-length, including signal peptide, naturally occurring CD16 that has a phenylalanine at position 176 of the full-length CD16 (which corresponds to position 158 of the mature CD16 protein). In some embodiments, a polynucleotide encoding a CD16 polypeptide has at least about 70% polynucleotide sequence identity with a polynucleotide sequence encoding a full-length, including the signal peptide, naturally occurring CD16 that has a valine at position 176 (which corresponds to position 158 of the mature protein). In some embodiments, a polynucleotide encoding CD16 has at least 70% identity to SEQ ID NO:5 and comprises a codon encoding valine at the position of the polynucleotide that encodes position 176 of the full-length, including the signal peptide, CD16 polypeptide. In some embodiments, a polynucleotide encoding CD16 has at least 90% identity to SEQ ID NO:5 and comprises a codon encoding valine at position 176 of the full-length CD16. In some embodiments, a polynucleotide encoding CD16 comprises SEQ ID NO:5, but with a codon encoding valine at position 176 of the full-length CD16.

In some embodiments, the CD16 polynucleotide encodes a polypeptide having at least 70%, 80%, 90%, or 95% identity to SEQ ID NO:1 or SEQ ID NO:2. In some embodiments, the polynucleotide encodes a polypeptide having at least 70% identity, or at least 80% identity, to SEQ ID NO:2 and comprises a valine at position 158 as determined with reference to SEQ ID NO:2. In some embodiments, the polynucleotide encodes a polypeptide having at least 90% identity to SEQ ID NO:2 and comprises a valine at position 158 as determined with reference to SEQ ID NO:2. In some embodiments, the polynucleotide encodes a polypeptide having at least 95% identity to SEQ ID NO:2 and comprises a valine at position 2 as determined with reference to SEQ ID NO:2. In some embodiments the polynucleotide encodes SEQ ID NO:2. In some embodiments, a CD16 polynucleotide encodes an extracellular domain of CD16 with or without the signal sequence, or any other fragment of a full length CD16, or a chimeric receptor encompassing at least partial sequence of CD16 fused to an amino acid sequence of another protein. In other embodiments, an epitope tag peptide, such as FLAG, myc, polyhistidine, or V5 can be added to the amino terminal domain of the mature polypeptide to assist in cell surface detection by using anti-epitope tag peptide monoclonal or polyclonal antibodies.

In some embodiments, homologous CD16 polynucleotides may be about 150 to about 700, about 750, or about 800 polynucleotides in length, although CD16 variants having more than 700 to 800 polynucleotides are within the scope of the disclosure.

Homologous polynucleotide sequences include those that encode polypeptide sequences coding for variants of CD16. Homologous polynucleotide sequences also include naturally occurring allelic variations related to SEQ ID NO:5. Transfection of an NK-92 cell with any polynucleotide encoding a polypeptide having the amino acid sequence shown in either SEQ ID. NO: 1 or SEQ ID NO: 2, a naturally occurring variant thereof, or a sequence that is at least 70% identical, or at least 80%, 90%, or 95% identical to SEQ ID. NO: 1 or SEQ ID NO: 2 is within the scope of the disclosure. In some embodiments, homologous polynucleotide sequences encode conservative amino acid substitutions in SEQ ID. NO: 1 or SEQ ID NO: 2. In some embodiments, NK-92 cells are transfected using a degenerate homologous CD16 polynucleotide sequence that differs from a native polynucleotide sequence, but encodes the same polypeptide.

In other examples, cDNA sequences having polymorphisms that change the CD16 amino acid sequences are used to modify the NK-92 cells, such as, for example, the allelic variations among individuals that exhibit genetic polymorphisms in CD16 genes. In other examples, CD16 genes from other species that have a polynucleotide sequence that differs from the sequence of SEQ ID NO:5 are used to modify NK-92 cells.

In examples, variant polypeptides are made using methods known in the art such as oligonucleotide-mediated (site-directed) mutagenesis, alanine scanning, and PCR mutagenesis. Site direct mutagenesis (Carter, 1986; Zoller and Smith, 1987), cassette mutagenesis, restriction selection mutagenesis (Wells et al., 1985) or other known techniques can be performed on the cloned DNA to produce CD16 variants (Ausubel, 2002; Sambrook and Russell, 2001).

In some embodiments, a polynucleotide encoding a CD16 is mutated to alter the amino acid sequence encoding for CD16 without altering the function of CD16. For example, polynucleotide substitutions leading to amino acid substitutions at "non-essential" amino acid residues can be made in SEQ ID NO:1 or SEQ ID NO:2.

Conservative substitutions in SEQ ID. NO:1 or SEQ ID NO:2, whereby an amino acid of one class is replaced with another amino acid of the same class, fall within the scope of the disclosed CD16 variants as long as the substitution does not materially alter the activity of the polypeptide. Conservative substitutions are well known to one of skill in the art. Non-conservative substitutions that affect (1) the structure of the polypeptide backbone, such as a β-sheet or α-helical conformation, (2) the charge, (3) the hydrophobicity, or (4) the bulk of the side chain of the target site can modify CD16 polypeptide function or immunological identity. Non-conservative substitutions entail exchanging a member of one of these classes for another class. Substitutions may be introduced into conservative substitution sites or more preferably into non-conserved sites.

In some embodiments, CD16 polypeptide variants are at least 200 amino acids in length and have at least 70% amino acid sequence identity, or at least 80%, or at least 90% identity to SEQ ID NO:1 or SEQ ID NO:2. In some embodiments, CD16 polypeptide variants are at least 225 amino acid in length and have at least 70% amino acid sequence identity, or at least 80%, or at least 90% identity to SEQ ID NO:1 or SEQ ID NO:2. In some embodiments, CD16 polypeptide variants have a valine at position 158 as determined with reference to SEQ ID NO:2.

In some embodiments a nucleic acid encoding a CD16 polypeptide may encode a CD16 fusion protein. A CD16 fusion polypeptide includes any portion of CD16 or an entire CD16 fused with a non-CD16 polypeptide. Fusion polypeptides are conveniently created using recombinant methods. For example, a polynucleotide encoding a CD16 polypeptide such as SEQ ID NO:1 or SEQ ID NO:2 is fused in-frame with a non-CD16 encoding polynucleotide (such as a polynucleotide sequence encoding a signal peptide of a heterologous protein). In some embodiment, a fusion polypeptide may be created in which a heterologous polypeptide sequence is fused to the C-terminus of CD16 or is positioned internally in the CD16. Typically, up to about 30% of the CD16 cytoplasmic domain may be replaced. Such modification can enhance expression or enhance cytotoxicity (e.g., ADCC responsiveness). In other examples, chimeric proteins, such as domains from other lymphocyte activating receptors, including but not limited to Ig-a, Ig-B, CD3-e, CD3-d, DAP-12 and DAP-10, replace a portion of the CD16 cytoplasmic domain.

Fusion genes can be synthesized by conventional techniques, including automated DNA synthesizers and PCR amplification using anchor primers that give rise to complementary overhangs between two consecutive gene fragments that can subsequently be annealed and reamplified to generate a chimeric gene sequence (Ausubel, 2002). Many vectors are commercially available that facilitate sub-cloning CD16 in-frame to a fusion moiety.

Cytokines

The cytotoxicity of NK-92 cells is dependent on the presence of cytokines (e.g., interleukin-2 (IL-2)). The cost of using exogenously added IL-2 needed to maintain and expand NK-92 cells in commercial scale culture is significant. The administration of IL-2 to human subjects in sufficient quantity to continue activation of NK92 cells would cause adverse side effects.

In some embodiments, FcR-expressing NK-92 cells are further modified to express at least one cytokine and a suicide gene. In specific embodiments, the at least one cytokine is IL-2, IL-12, IL-15, IL-18, IL-21 or a variant thereof. In preferred embodiments, the cytokine is IL-2. In certain embodiments the IL-2 is a variant that is targeted to the endoplasmic reticulum, and the suicide gene is inducible caspase 9.

In one embodiment, the IL-2 is expressed with a signal sequence that directs the IL-2 to the endoplasmic reticulum. In some embodiments, a polynucleotide that encodes IL-2 encodes a polypeptide having a sequence of SEQ ID NO:7. Not to be bound by theory, but directing the IL-2 to the endoplasmic reticulum permits expression of IL-2 at levels sufficient for autocrine activation, but without releasing IL-2 extracellularly. See Konstantinidis et al "Targeting IL-2 to the endoplasmic reticulum confines autocrine growth stimulation to NK-92 cells" *Exp Hematol.* 2005 February; 33(2): 159-64. Continuous activation of the FcR-expressing NK-92 cells can be prevented, e.g., by the presence of the suicide gene.

Immunotherapy

Antibodies may be used to target cells that are infected or express cancer-associated markers. A number of antibodies have been approved for the treatment of cancer, alone.

TABLE 2

Illustrative therapeutic monoclonal antibodies
Examples of FDA-approved therapeutic monoclonal antibodies

| Antibody | Brand name | Company | Target | Indication (Targeted disease) |
|---|---|---|---|---|
| Alemtuzumab | Campath ® | Genzyme | CD52 | Chronic lymphocytic leukemia |
| Brentuximab vedotin | Adcetris ® | | CD30 | Anaplastic large cell lymphoma (ALCL) and Hodgkin lymphoma |
| Cetuximab | Erbitux ® | Bristol-Myers Squibb/Eli Lilly/Merck KGaA | epidermal growth factor receptor | Colorectal cancer, Head and neck cancer |
| Gemtuzumab | Mylotarg ® | Wyeth | CD33 | Acute myelogenous leukemia (with calicheamicin) |
| Ibritumomab tiuxetan | Zevalin ® | Spectrum Pharmaceuticals, Inc. | CD20 | Non-Hodgkin lymphoma (with yttrium-90 or indium-111) |
| Ipilimumab (MDX-101) | Yervoy ® | | blocks CTLA-4 | Melanoma |
| Ofatumumab | Arzerra ® | | CD20 | Chronic lymphocytic leukemia |
| Palivizumab | Synagis ® | MedImmune | an epitope of the RSV F protein | Respiratory Syncytial Virus |
| Panitumumab | Vectibix ® | Amgen | epidermal growth factor receptor | Colorectal cancer |
| Rituximab | Rituxan ® Mabthera ® | Biogen Idec/Genentech | CD20 | Non-Hodgkin lymphoma |
| Tositumomab | Bexxar ® | GlaxoSmithKline | CD20 | Non-Hodgkin lymphoma |
| Trastuzumab | Herceptin ® | Genentech | ErbB2 | Breast cancer |
| Blinatumomab | | | bispecific CD19-directed CD3 T-cell engager | Philadelphia chromosome-negative relapsed or refractory B cell precursor acute lymphoblastic leukemia (ALL) |
| Avelumab | | | anti-PD-L1 | Non-small cell lung cancer, metastatic Merkel cell carcinoma, gastric cancer, breast cancer, ovarian cancer, bladder cancer, melanoma, mesothelioma, including metastatic or locally advanced solid tumors |
| Daratumumab | | | CD38 | Multiple myeloma |
| Elotuzumab | | | a SLAMF7-directed (also known as CD 319) immunostimulatory antibody | Multiple myeloma |

Antibodies may treat cancer through a number of mechanisms. Antibody-dependent cellular cytotoxicity (ADCC) occurs when immune cells, such as NK cells, bind to antibodies that are bound to target cells through Fc receptors, such as CD16.

Accordingly, in some embodiments, NK-92 cells that express CD16 are administered to a patient along with antibodies directed against a specific cancer-associated protein.

Administration of the FcR-expressing NK-92 cells may be carried out simultaneously with the administration of the monoclonal antibody, or in a sequential manner. Genetic modification of the NK-92 cells to express the FcR enables the cells to recognize Ab-coated target cells and trigger NK cell-mediated ADCC, thus resulting in rapid NK-cell activation. In some embodiments, the FcR-expressing NK-92 cells are administered to the subject after the subject has been treated with the monoclonal antibody. In some embodiments, the FcR-expressing NK-92 cells are administered within 24 hours, or within 18 hours, or within 12 hours, or within 8 hours or within 6, 5, 4, 3, 2, or 1 hours of administering the monoclonal antibody. In some embodiments, the FcR-expressing NK-92 cells are administered from 24 to 72 hours after administration of the antibody. In some embodiments, the FcR-expressing NK-92 cells are administered within 1, 2, 3, or 4 days, or greater, of administering the antibody.

In some embodiments, the FcR-expressing NK-92 cells and monoclonal antibody are administered intravenously. In some embodiments the FcR-expressing NK-92 cells are infused directly into the bone marrow.

In one aspect of the invention, the FcR-expressing NK-92 cells are administered to a subject suffering from leukemia combination with a therapeutic monoclonal antibody, e.g., alemtuzumab. In some embodiments, the FcR-expressing NK-92 cells are administered simultaneously with alemtuzumab. In some embodiments, the FcR-expressing NK-92 cells are administered after the subject has been treated with alemtuzumab. In some embodiments, the FcR-expressing NK-92 cells are administered within 24 hours, or within 18 hours, or within 12 hours, or within 8 hours or within 6, 5, 4, 3, 2, or 1 hour of administration of alemtuzumab. In some embodiments, the FcR-expressing NK-92 cells are administered 24 to 72 hours, or longer, following administration of alemtuzumab.

In a further aspect, the FcR-expressing NK-92 cells are administered in combination with trastuzumab to a subject suffering from a cancer such as breast cancer or stomach cancer. In some embodiments, the FcR-expressing NK-92 cells are administered simultaneously with trastuzumab. In some embodiments, the FcR-expressing NK-92 cells are administered after trastuzumab. In some embodiments, the FcR-expressing NK-92 cells are administered within 24 hours, or within 18 hours, or within 12 hours, or within 8 hours or within 6, 5, 4, 3, 2, or 1 hour of administration of trastuzumab. In some embodiments, the FcR-expressing NK-92 cells are administered 24 to 72 hours, or longer, following administration of trastuzumab.

In an additional aspect, the FcR-expressing NK-92 cells are administered to a subject suffering from Hodgkin lymphoma in combination with brentuximab. In some embodiments, the FcR-expressing NK-92 cells are administered simultaneously with brentuximab. In some embodiments, the FcR-expressing NK-92 cells are administered after brentuximab. In some embodiments, the FcR-expressing NK-92 cells are administered within 24 hours, or within 18 hours, or within 12 hours, or within 8 hours or within 6, 5, 4, 3, 2, or 1 hour of administration of brentuximab. In some embodiments, the FcR-expressing NK-92 cells are administered 24 to 72 hours, or longer, following administration of brentuximab.

In an additional aspect, the FcR-expressing NK-92 cells are administered to a subject suffering from multiple myeloma in combination with daratumumab. In some embodiments, the FcR-expressing NK-92 cells are administered simultaneously with daratumumab. In some embodiments, the FcR-expressing NK-92 cells are administered after daratumumab. In some embodiments, the FcR-expressing NK-92 cells are administered within 24 hours, or within 18 hours, or within 12 hours, or within 8 hours or within 6, 5, 4, 3, 2, or 1 hour of administration of daratumumab. In some embodiments, the FcR-expressing NK-92 cells are administered 24 to 72 hours, or longer, following administration of daratumumab.

Transgene Expression

Transgenes (e.g. CD16 and IL-2) can be engineered into an expression plasmid by any mechanism known to those of skill in the art. Transgenes may be engineered into the same expression plasmid or different. In preferred embodiments, the transgenes are expressed on the same plasmid.

Transgenes can be introduced into the NK-92 cells using any transient transfection method known in the art, including, for example, electroporation, lipofection, nucleofection, or "gene-gun."

Any number of vectors can be used to express CD16 and IL-2. In some embodiments, the vector is a retroviral vector. In some embodiments, the vector is a plasmid vector. Other viral vectors that can be used include adenoviral vectors, adeno-associated viral vectors, herpes simplex viral vectors, pox viral vectors, and others.

NK-92 cells can be administered to such an individual by absolute numbers of cells, e.g., said individual can be administered from about 1000 cells/injection to up to about 10 billion cells/injection, such as at about, at least about, or at most about, $1\times10^8$, $1\times10^7$, $5\times10^7$, $1\times10^6$, $5\times10^6$, $1\times10^5$, $5\times10^5$, $1\times10^4$, $5\times10^4$, $1\times10^3$, $5\times10^3$ (and so forth) NK-92 cells per injection, or any ranges between any two of the numbers, end points inclusive. In other embodiments, NK-92 cells can be administered to such an individual by relative numbers of cells, e.g., said individual can be administered about 1000 cells to up to about 10 billion cells per kilogram of the individual, such as at about, at least about, or at most about, $1\times10^8$, $1\times10^7$, $5\times10^7$, $1\times10^6$, $5\times10^6$, $1\times10^5$, $5\times10^5$, $1\times10^4$, $5\times10^4$, $1\times10^3$, $5\times10^3$ (and so forth) NK-92 cells per kilogram of the individual, or any ranges between any two of the numbers, end points inclusive. In some embodiments, between about 1 billion and about 3 billion NK-92 cells are administered to a patient. In other embodiments, the total dose may be calculated based on $m^2$ of body surface area, including $11\times10^{11}$, $1\times10^{10}$, $1\times10^9$, $1\times10^8$, $1\times10^7$, per $m^2$. The average person is 1.6-1.8 $m^2$.

The NK-92 cells, monoclonal antibody and/or other anti-cancer agents as described below, can be administered once to a patient with cancer or infected with a virus or can be administered multiple times, e.g., once every 1, 2, 3, 4, 5, 6, 7, 8, 9, 10, 11, 12, 13, 14, 15, 16, 17, 18, 19, 20, 21, 22 or 23 hours, or once every 1, 2, 3, 4, 5, 6 or 7 days, or once every 1, 2, 3, 4, 5, 6, 7, 8, 9, 10 or more weeks during therapy, or any ranges between any two of the numbers, end points inclusive.

EXAMPLES

The following examples are for illustrative purposes only and should not be interpreted as limitations of the claimed invention. There are a variety of alternative techniques and procedures available to those of skill in the art which would similarly permit one to successfully perform the intended invention.

Example 1: CD16 Recombinant Retrovirus Preparation

CD16 cDNA X52645.1 encoding the low affinity mature form (SEQ ID NO:1) of the transmembrane immunoglobulin γ Fc region receptor III-A (FcγRIII-A or CD16) [Phenylalanine-158 (F158), complete sequence: SwissProt P08637 (SEQ ID NO:3)] or a polymorphic variant encoding a higher affinity mature form of the CD16 receptor [Valine-158 (F158V) (SEQ ID NO:2), complete sequence: SwissProt VAR 008801 (SEQ ID NO:4)] was sub-cloned into the bi-cistronic retroviral expression vector, pBMN-IRES-EGFP (obtained from G. Nolan, Stanford University, Stanford, Calif.) using the BamHI and NotI restriction sites in accordance with standard methods.

The recombinant vector was mixed with 10 µL of PLUS™ Reagent (Invitrogen; Carlsbad, Calif.); diluted to 100 µL with pre-warmed, serum-free Opti-MEM® (Invitrogen; MEM, minimum essential media); further diluted by the addition of 8 µL Lipofectamine™ (Invitrogen) in 100 µL pre-warmed serum-free Opti-MEM®; and incubated at room temperature for 15 minutes. This mixture was then brought to a total volume of 1 mL by the addition of pre-warmed serum-free Opti-MEM®. Phoenix-Amphotropic packaging cells (obtained from G. Nolan, Stanford University, Stanford, Calif.; (Kinsella and Nolan, 1996)) were grown to 70-80% confluence in a 6-well plate and washed with 6 mL of pre-warmed serum-free Opti-MEM® medium (Invitrogen). After removal of the medium, 1 mL of the solution of recombinant vector in Lipofectamine™ PLUS™ Reagent was added to each well, and the cells were incubated for at least three hours at 37° C. under a 7% $CO_2$/balance air atmosphere. Four mL of pre-warmed RPMI medium containing 10% fetal bovine serum (FBS) was added to each well, and the cells incubated overnight at 37° C., under a 7% $CO_2$/balance air atmosphere. The medium was then removed; the cells washed with 6 mL pre-warmed serum-free Opti-MEM®; 2 mL serum-free Opti-MEM® added; and the cells incubated at 37° C., under a 7% $CO_2$/balance air atmosphere for an additional 48 hours.

The virus-containing supernatant was collected into a 15 mL plastic centrifuge tube; centrifuged at 1300 rpm for 5 minutes to remove cells and cell fragments; and the supernatant transferred to another 15 mL plastic centrifuge tube. Immediately before use, 20 µL of PLUS™ Reagent was added to the virus suspension; the mixture incubated at room temperature for 15 minutes; 8 µL Lipofectamine™ added to the mixture; and the mixture incubated for an additional 15 minutes at room temperature.

Example 2: Cloning the IL-2 Gene and the TK Suicide Gene into the CD16 Recombinant Retrovirus The thymidine kinase (TK) gene and a KDEL-tagged construct generating ER-resident IL-2 (Konstantinidis et al. 2005 *Experimental Hematology* 33: 159-64) are used to prepare recombinant retroviruses incorporating the gene for the expression of IL-2 and ligate the corresponding cDNAs into the CD16 pBMN-IRES-EGFP vector (Miah and Campbell 2010 *Methods Mol. Biol.* 612: 199-208). The pBMN-IRES-EGFP vector is then transfected into the Phoenix-Amphotropic packaging cell line in the presence of Lipofectamine™ Plus as described in Example 1.

Example 3: Retroviral Transduction of TK, CD16 and IL-2 into NK-92 Cells

NK-92 cells cultured in A-MEM (Sigma; St. Louis, Mo.) supplemented with 12.5% FBS, 12.5% fetal horse serum (FHS) and 500 IU rhIL-2/mL (Chiron; Emeryville, Calif.) are collected by centrifugation at 1300 rpm for 5 minutes, and the cell pellet re-suspended in 10 mL serum-free Opti-MEM® medium. An aliquot of cell suspension containing $5 \times 10^4$ cells is sedimented at 1300 rpm for 5 minutes; the cell pellet re-suspended in 2 mL of the retrovirus suspension described in Example 1, and the cells plated into 12-well culture plates. The plates are centrifuged at 1800 rpm for 30 minutes and incubated at 37° C. under an atmosphere of 7% $CO_2$/balance air for 3 hours. This cycle of centrifugation and incubation is repeated a second time. The cells are diluted with 8 mL of α-MEM, transferred to a T-25 flask, and incubated at 37° C. under a 7% $CO_2$/balance air until the cells are confluent. The transduced cells are collected, re-suspended in serum-free Opti-MEM® medium, and sorted on the basis of their level of EGFP expression using a fluorescence activated cell sorter (FACS), EGFP being co-expressed with, and a surrogate marker for, CD16. Cell-surface expression of CD16 is confirmed by immuno-staining the transduced cells with an anti-CD16 antibody. Cell-surface expression of IL-2 is determined by immuno-staining with purified rat anti-human IL-2 antibody, and IL-2 intracellular localization was confirmed by immune-staining with rabbit anti-calreticulin ER-Marker. The transduced cells, designated as NK-92-TK-CD16-IL2, are assayed for cell-surface expression of CD16 and IL-2 intracellular expression before use. The cells are assayed for expression of TK by testing for sensitivity to ganciclovir.

Example 4: Growth of NK-92-TK-CD16-IL-2 and Non-Modified NK-92 Cells in the Presence or Absence of Exogenous IL-2

NK-92-TK-CD16-IL-2 and non-modified NK-92 cells are initially cultured in the presence of exogenous IL-2 (1,200 IU/mL) for 4 to 5 weeks, and then transferred to an IL-2-free medium and cultured in the absence of exogenous IL-2. Proliferation of these cells is then assessed.

Surface expression of CD16 and IL-2 is measured by flow cytometry. Flow cytometric analysis performed after 24 hours incubation of NK-92-TK-CD16-IL-2 and non-modified NK-92 cells in the absence of exogenous IL-2 shows similar cytotoxic action in NK-92-TK-CD16-IL-2 and non-modified NK-92 cells, with the NK-92-TK-CD16-IL-2 cells presenting increased CD16 surface expression and much lower surface expression of IL-2 as compared to non-modified NK-92 cells.

These results are confirmed by experiments that determine whether the NK-92-TK-CD16-IL-2 cells support growth of bystander non-modified NK-92 cells, in which the non-modified NK-92 cells are mixed with NK-92-TK-CD16-IL-2 and co-cultured in the absence of exogenous IL-2. These experiments show that the NK-92-TK-CD16-IL-2 do not support the growth of non-modified NK-92 cells because of minimal release of IL-2 into the medium. In fact, the non-modified NK-92 cells stop proliferating after 48 hours incubation in the absence of exogenous IL-2. In contrast, proliferation of NK-92-TK-CD16-IL-2 cells is still visible after 72 hours incubation.

Overall, these results show that ER-IL-2 stimulates the growth of NK-92-TK-CD16-IL-2 cells when these cells are maintained in an environment not containing exogenous IL-2.

Example 5: Systemic Toxicity and Expansion of NK-92-TK-CD16-IL-2 Cells is Effectively Eliminated by the Suicide Gene Endogenous expression of IL-2 may lead to the potential development of killer cell mutants with autonomous growth. In vivo expansion of NK-92-TK-CD16-IL-2 cells, NK-92-TK-CD16-IL-2 cells and non-modified NK-92 cells is therefore evaluated. SCID mice are sub-lethally irradiated (250 rad) and separated into two groups. Between 15 and 20 days later, when the tumor is palpable (0.5-0.8 cm in diameter), NK-92-TK-CD16-IL-2 cells are injected intravenously into the first group of irradiated mice, and non-modified NK-92 cells are injected intravenously into the second group of mice. No exogenous cytokines are administered to the mice. Detection of EGFP expression with a fluorescence activated cell sorter (FACS) is used to monitor localization and expansion. Both groups of mice show targeted localization and expansion 24 hours after injection. After 24 hours, the non-modified NK-92 cells in the control mice group stop expanding, whereas the NK-92-TK-CD16-IL-2 cells continue to expand significantly. Forty-eight hours after injection apoptosis of non-modified NK cells in the control mice and exponential expansion of NK-92-TK-CD16-IL-2 cells in the test group of mice are visible. In control mice the tumor quickly reaches a size equal to or greater than 1.2 cm in diameter, and the mice are euthanized.

Mice from the test group with smaller tumors or complete tumor regression are segregated into two groups to evaluate the functionality of the suicide gene. The mice in the first group are treated with two or three doses of ganciclovir (50 µg) intraperitoneally every other day. The mice in the second group are treated with placebo. Administration of ganciclovir to the mice leads to a significant reduction in NK-92-TK-CD16-IL-2 cells within 24 hours to 72 hours, with the cells returning to a pre-expansion level. Expansion of NK-92-TK-CD16-IL-2 cells continues to increase over time in mice treated with placebo.

These results show that the presence of the TK gene ensures that the NK-92-TK-CD16-IL-2 remain sensitive to ganciclovir and prevents exponential expansion of NK-92-TK-CD16-IL-2 cells. Thus, the combination of TK and IL-2 on the same retroviral vector, incorporated into the chromosome of NK92 cells, provides enhanced biological safety. Because the cells are dependent on IL-2, there is a strong selection for retaining the TK-CD16-IL-2 sequence. As such, the cells are sensitive to ganciclovir. Those cells that lose the TK gene, and become resistant to ganciclovir, would also have lost the IL-2 gene that is necessary for their growth.

Example 6: Cytotoxic Activity of NK-92-TK-CD16-IL-2 Against Different Leukemic Cell Lines NK-92-TK-CD16-IL-2 effector cells are washed by suspension in α-MEM (without IL-2) and sedimented at 1300 rpm for 5 minutes. The cell pellet is suspended in α-MEM, cells counted, and aliquots prepared at cell concentrations of $1\times10^5$/mL (effector to target cell ratio (E:T)=1:1), $5\times10^5$/mL (E:T=5:1), $1\times10^6$/mL (E:T=10:1), $2\times10^6$/mL (E:T=20:1) or as appropriate to the determination being performed.

The cytotoxic activity of NK-92-TK-CD16-IL-2 effector cells against K562, Daudi, TF-1, AML-193, and SR-91 cells is determined (Gong et al. (1994)). K562 (erythroleukemia) and Daudi (Burkitt) lymphoma cell lines are obtained from ATCC. They are maintained in continuous suspension culture in RPMI 1640 medium supplemented with 10% fetal calf serum (FCS). TF-1 is a myelomonocytic cell line (Kitamura et al., *J. Cell Physiol.* 140:323-334 (1989)) that requires the presence of medium containing 2 ng/mL of human GM-CSF. AML-193 is a myeloid cell line that is maintained in the presence of 10% 5637-conditioned medium (Lange et al., *Blood* 70:192-199 (1987)). Both TF-1 and AML-193 cells are obtained from Dr. D. Hogge, Terry Fox Laboratory, University of British Columbia, Vancouver, BC. SR-91 is a cell line with features of early progenitor cells established by Gong et al. (1994) from a patient with acute lymphoblastic leukemia (ALL) (Klingemann et al., *Leuk. Lymphoma,* 12, 463-470 (1994). It is resistant to both NK and activated-NK (A-NK) cell cytotoxicity. SR-91 is also maintained in RPMI 1640/10% FCS. This cell line can be rendered sensitive to killing by NK-92 by treatment with cytokine.

The cytotoxic activity of the NK-92-TK-CD16-IL-2 effector cells against these target cells is measured in triplicates in a standard 4-hour $^{51}$Cr-release assay in triplicate. Briefly, $1\times10^6$ NK-92-TK-CD16-IL-2 cells are labeled with 100 μL 51Cr (specific activity of 1 mCi/mL) and incubated for one hour at 37° C. Effector cells are counted using trypan blue dye exclusion and mixed with target cells to obtain an effector:target ratio of 10:1, 3:1, 1:1, and 0.3:1. CellGro medium is used as a negative control, and for positive control, cells are incubated with 1% Triton X. After incubation in a V-bottom-shaped 96-well plate for 4 hours at 37° C., 70 μL of supernatant is aspirated from each well and counted using a Packard Cobra Auto-Gamma 5000 Series counting system (Meriden, Conn., USA). The percentage of spontaneous release is calculated from the following formula: % specific 51Cr release=(sample release−spontaneous release)/(maximum release−spontaneous release)×100.

The cytotoxic activity of NK-92-TK-CD16-IL-2 cells against K562 and Daudi cells is significantly higher than the cytotoxic activity of non-modified NK cells-92. The cytolytic activity of NK-92-TK-CD16-IL-2 cells against TF-1 cells and AML-193 cells is less potent but still higher than the cytolytic activity of non-modified NK-92 cells. SR-91 cells are resistant to the cytotoxic effect of both the NK-92-TK-CD16-IL-2 cells and the non-modified NK-92 cells. This lack of cytotoxic activity against SR-91 cells is consistent with the lack in SR-91 cells of adhesion molecules necessary to mediate initial binding with NK-92 cells.

Example 7: Cytolysis of Human Primary Leukemic Cells by NK-92-TK-CD16-IL-2 Cells Samples are obtained, with informed consent, during routine diagnostic blood studies or bone marrow (BM) aspirates from patients with newly diagnosed or relapsed leukemias. Blast-enriched mononuclear cells are isolated by Ficoll Hypaque (Pharmacia, Piscataway, N.J.) density gradient separation and washed in RPMI 1640 medium. NK-92-TK-CD16-IL-2 cells and non-modified NK-92 cells are cultured and maintained in α-MEM medium supplemented with 12.5% FCS and 12.5% horse serum. The cytotoxic activity of NK-92-TK-CD16-IL-2 cells and non-modified NK-92 cells on the leukemic samples is then compared using a standard 4-hour chromium release assay.

The cytolytic activity of NK-92-TK-CD16-IL-2 cells against leukemic targets is significantly higher than that of non-modified NK-92 cells. The NK-92-TK-CD16-IL-2 cells of the invention are surprisingly and significantly more effective in lysing patient-derived tumor cells, and exert their effect in a shorter time than non-modified NK-92 cells.

Example 8: Antileukemia Effect of NK-92-TK-CD16-IL-2 Cells in Human Leukemia Xenograft SCID Mice Model For study of the in vivo tumoricidal capacity of NK-92-TK-CD16-IL-2 cells, leukemic cells derived from a T-lineage-acute lymphoblastic leukemia (ALL) patient, an acute myeloid leukemia (AML) patient, and a pre-B-ALL patient are adoptively grown and expanded in SCID mice by S.C. inoculation. Leukemic cells recovered from the leukemic nodules in the mice (first passage) are used in these experiments. The SCID mice in each group are inoculated I.P. with $5\times10^6$ leukemic cells from the first passage in 0.2 mL PBS, and 24 hours later $2\times10^7$ NK-92-TK-CD16-IL-2 cells in 0.4 mL PBS are administered by I.P. injection. The animals receive either 1 dose or a series of 5 doses of NK-92-TK-CD16-IL-2 cells which are administered on days 1, 3, 5, 7, and 9, with and without exogenous IL-2.

All the human leukemias grow aggressively in SCID mice. Leukemic cells derived from the T-ALL patient, the AML patient and the pre-B-ALL patient are highly sensitive in vitro to the NK-92-TK-CD16-IL-2 cells, and non-modified NK-92 cells.

Treatment with NK-92-TK-CD16-IL-2 cells significantly prolong the life and extend survival of the mice compared to treatment with non-modified NK-92 cells. Several animals that received 5 doses of NK-92-TK-CD16-IL-2 cell injections survive without any signs of leukemia development 6 months after inoculation. Mice treated with NK-92 show initial improvement but leukemic cells are observed in a minority of mice at 6 months.

These results show that in vivo treatment of leukemic tumors with NK-92-CD16-IL-2 cells is very effective and results in prolongation of life and health improvement.

Example 9: ADCC Mediated Cell Lysis

The activity of several antibodies that are highly selective and effective anti-tumor agents depends at least in part on the binding of natural killer cells to the Fc (constant) portion of the antibody, such that lysis of tumor cells occurs via an antibody-dependent cellular cytotoxicity (ADCC) mechanism. Although NK-92 cells retain almost all of the activating receptors and cytolytic pathways associated with NK cells, they do not express the CD16 receptor and, therefore, cannot lyse target cells via the ADCC mechanism. Transgenic insertion of CD16 expression into NK-92 cells allows NK-92 cells to act via the ADCC mechanism if the cells have sufficient binding affinity for an effective antibody.

The effect of binding to different antibodies is evaluated in FcR-expressing NK-92 cells that are administered to a subject suffering from leukemia 24 to 72 hours after the subject has been treated with Alemtuzumab. FcR-expressing NK-92 cells and the cytotoxic effect of antibody binding on target cancer cells is compared to the cytotoxic effect of non-modified NK-92 cells. The antibodies and corresponding target cancer cells are selected and assayed according to Table 2.

The selected target cells are labeled with Na [$^{51}$Cr] chromate. Aliquots of the $^{51}$[Cr]-labeled target cells are further incubated with the selected antibody at multiple concentrations between 0.01 µg and 5 µg/mL for 15 minutes at room temperature, washed with α-MEM, and adjusted to a concentration of $1\times10^5$ cells/mL before use. One-hundred µL of the selected type of target cells and 100 µL of effector cells at cell concentrations of $1\times10^5$ cells/mL (E:T=1:1), $5\times10^5$ cells/mL (E:T=5:1), $1\times10^6$ cells/mL (E:T=10:1), $2\times10^6$ cells/mL (E:T=20:1) or as appropriate to the determination being performed are added to each well of a 96-well V-bottom plate. Three to six replicate wells are prepared at each E:T ratio to be evaluated. At least 6 wells are allocated to each of a spontaneous lysis control (effector cells replaced with 100 µL of α-MEM) and total release control (effector cells replaced with 100 µL of 2% Triton X-100 detergent in α-MEM). An additional three wells at each E:T ratio are allocated to "non-ADCC" controls in which the target cells were not exposed to the antibody. An additional 6 or more wells are allocated to the use of unmodified NK-92 effector cells that do not express CD16 as a procedural control and internal standard. The plate is then centrifuged at 500 rpm for 3 minutes and incubated for 4 hours at 37° C. in an atmosphere of 7% $CO_2$/balance air. At the end of the incubation period, the plate is centrifuged at 1500 rpm for 8 minutes and 100 mL of the supernatant is collected from each well for counting in a γ counter as a measure of $^{51}$[Cr] release due to cytotoxicity. The percentage of specific lysis is then calculated.

These assays are repeated with FcR-expressing NK-92 cells expressing varying surface levels of CD16.

FcR-expressing NK-92 cells show high cytotoxic activity against the target cancer cells in the presence of the selected antibody. Non-modified NK-92 cells show lower cytotoxic activity against the target cancer cells. These results demonstrate that the FcR-expressing NK-92 cells have the ability to act via the ADCC mechanism and thus provide enhanced therapeutic effect against tumor cells in the presence of the antibodies.

Example 10: Combined Antileukemia Effect of FcR-Expressing NK-92 Cells and Gemtuzumab in Human Leukemia Xenograft SCID Mice Model For study of the in vivo tumoricidal capacity of FcR-expressing NK-92 cells, leukemic cells derived from an acute myeloid leukemia (AML) patient are adoptively grown and expanded in SCID mice by S.C. inoculation. Leukemic cells recovered from the leukemic nodules in the mice (first passage) are used in these experiments. The SCID mice in each group are inoculated I.P. with $5\times10^6$ leukemic cells from the first passage in 0.2 mL PBS, and 24 hours later $2\times10^7$ FcR-expressing NK-92 cells in 0.4 mL PBS and Gemtuzumab are administered by I.P. injection. The animals receive either 1 dose or a series of 5 doses of FcR-expressing NK-92 cells which are administered on days 1, 3, 5, 7, and 9, with or without Gemtuzumab. Control animals are treated with non-modified NK-92 cells with or without Gemtuzumab.

The human leukemias grow aggressively in SCID mice. Mice treated with the FcR-expressing NK-92 cells in combination with Gemtuzumab show tumor regression and the antitumorogenic effect is higher than in mice treated solely with the FcR-expressing NK-92 cells without Gemtuzumab, and more than the mice treated with NK-92.

These results show that in vivo treatment of leukemic tumors with FcR-expressing NK-92 cells in combination with monoclonal antibodies, such as Gemtuzumab, is very effective and results in prolongation of life and health improvement.

Example 11: Construction of a Plasmid Expression Vector Expression CD16 and Endoplasmic Reticulum-Targeted IL-2

The Gene String program of GeneArt (Life Technologies) was used to design a plasmid backbone de novo. Its minimal structure includes a colE1 bacterial origin of replication, an Ampicillin resistance cassette, and a mammalian expression cassette composed of an EF1α promoter and an SV40 polyadenylation site, flanking a multiple cloning site (MCS).

The mammalian expression cassette is flanked by BamHI sites that allow not only linearization of the plasmid but also the removal of all non-eukaryotic sequences.

The expressed transgene is the human CD16 158V sequence followed by an IRES sequence itself followed by the ERIL-2 sequence (IL-2 KDEL) such that the IL-2 is targeted to the endoplasmic reticulum. Both CD16 and ERIL-2 sequences were codon-optimized by GeneArt to maximize expression in a human. The transgene can be excised using EcoRI and NotI. The resulting mRNA is a bicistronic transcript under the control of the EF1α promoter, with the ERIL-2 translated independently from CD16, under the control of the IRES sequence. A schematic of the plasmid is provided in FIG. 1. This plasmid was used to transfect NK-92 cells.

Example 12: Transfection of NK-92.W Cells Using a Plasmid Expression Vector

NK-92.W cells is the parental line for most clinical trials to date. One vial of the Bioreliance working cell bank (WCB, p15 11/30/00) was thawed into a T25 flask with 12 ml X-Vivo10 5% HS+500 IU/ml rhIL-2, and passaged every 2-4 days (dilution ×2 to ×4 in fresh X-vivo10 5% HS+IL-2, total of 18-20 split/passages).

Figure 2A:
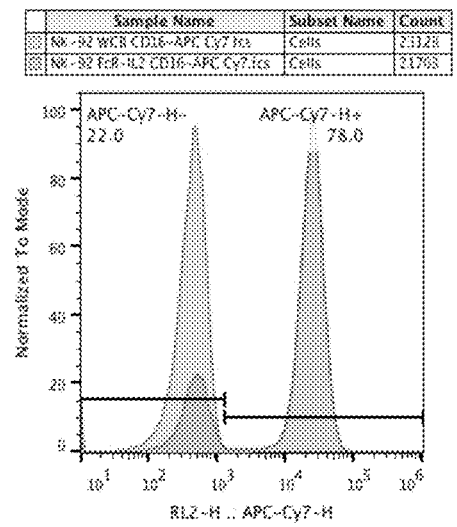
FIGS. 2a and 2b provide illustrative data showing expression of CD16 is NK-92 cells modified to express CD16 using a plasmid vector depicted in FIG. 1 at about 2 weeks (FIG. 2a) and about 4 weeks (FIG. 2b).
Figure 2B:
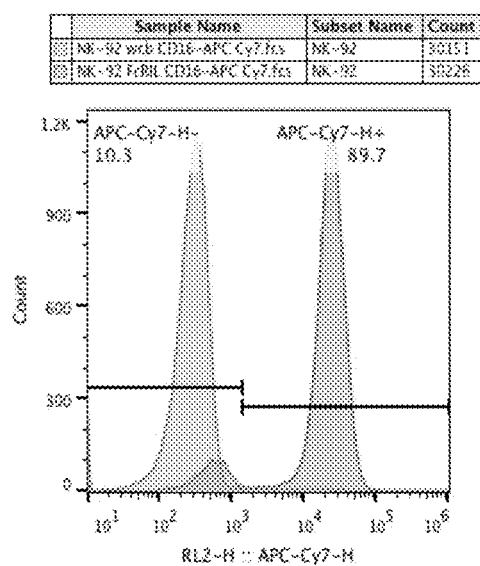

NK-92.W cells for transfection were spun at 500 g 10 min. The supernatant was discarded and the cells pellet was resuspended in 15 ml D-PBS 1× and centrifuged at 500 g 10 min. Pellet was resuspended in buffer R (Neon kit, Invitrogen) at a cell density of 10e7 cells/ml. NK-92.W cells were electroporated with pNEUKv1 CD16(158V)-ERIL2 plasmid, using a Neon electroporator (5 ug DNA for 10e6 cells in 100 ul buffer R; 1250V/10 ms/3 pulses with 3 ml buffer E2 in the electroporation tube). Electroporated cells were incubated overnight in medium+IL-2 (in 6-well plate, 4 ml medium/well), and transferred to medium without IL-2 on 10/16/14 (one PBS spin/wash). CD16 expression was assayed using an anti-CD16 antibody (clone 3G8, mouse IgGlk) APC-Cy7-conjugated (Bd Pharmingen). At just over two weeks, about 78% of the cells were CD16 positive (right peak, FIG. 2a). About 90% of the cells were positive at about four weeks (right peak, FIG. 2b).

NK-92.W CD16(158V)-ERIL2 cells were frozen (5 vials of ~1×10e6 cells/vial), and on 12/15/14 (5 vials of ~1×10e6 cells/vial).

Figure 3:
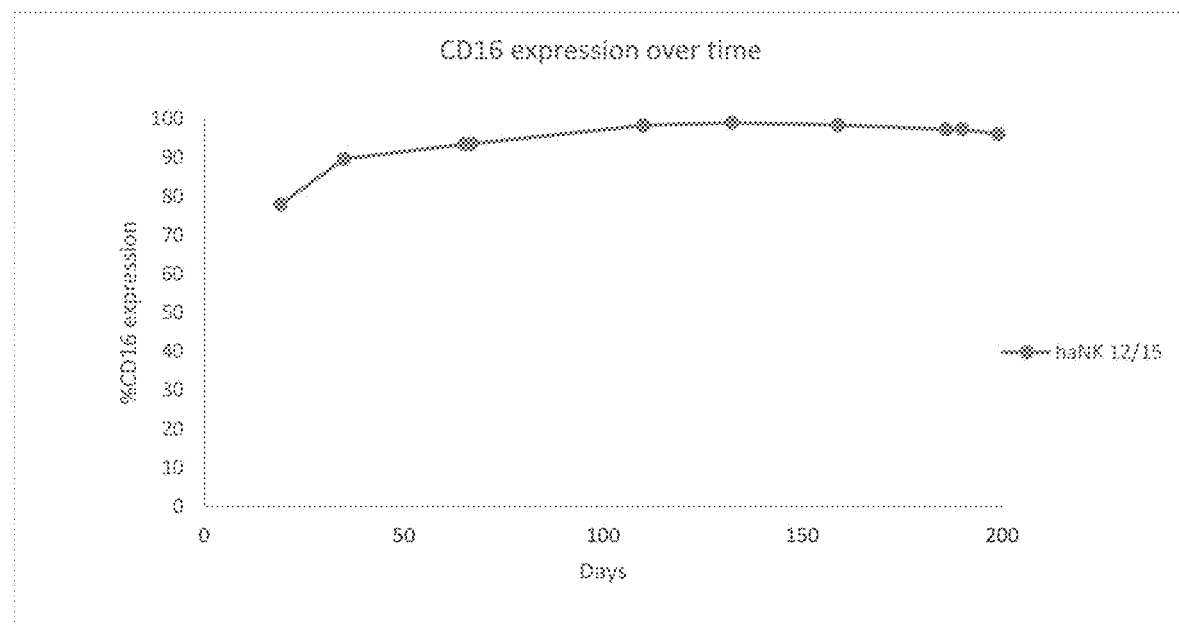
FIG. 3 provides illustrative data showing CD16 expression in modified NK-92 cells that were frozen for storing and then thawed for culture.

Frozen NK-92.W FcR-ERIL2 cells were evaluated. Cells were thawed and cultured in X-Vivo10 5% HS without IL-2 in a T25 flask. Expression of CD16(158V) was followed over time by flow cytometry (Attune) using the anti-CD16 antibody clone 3G8 conjugated to APC-Cy7, using the same settings to allow for comparison of MFI between assays. CD16 expressoin was stable over time (FIG. 3).

Example 13: Evaluation of ADCC Activity

Figure 4:
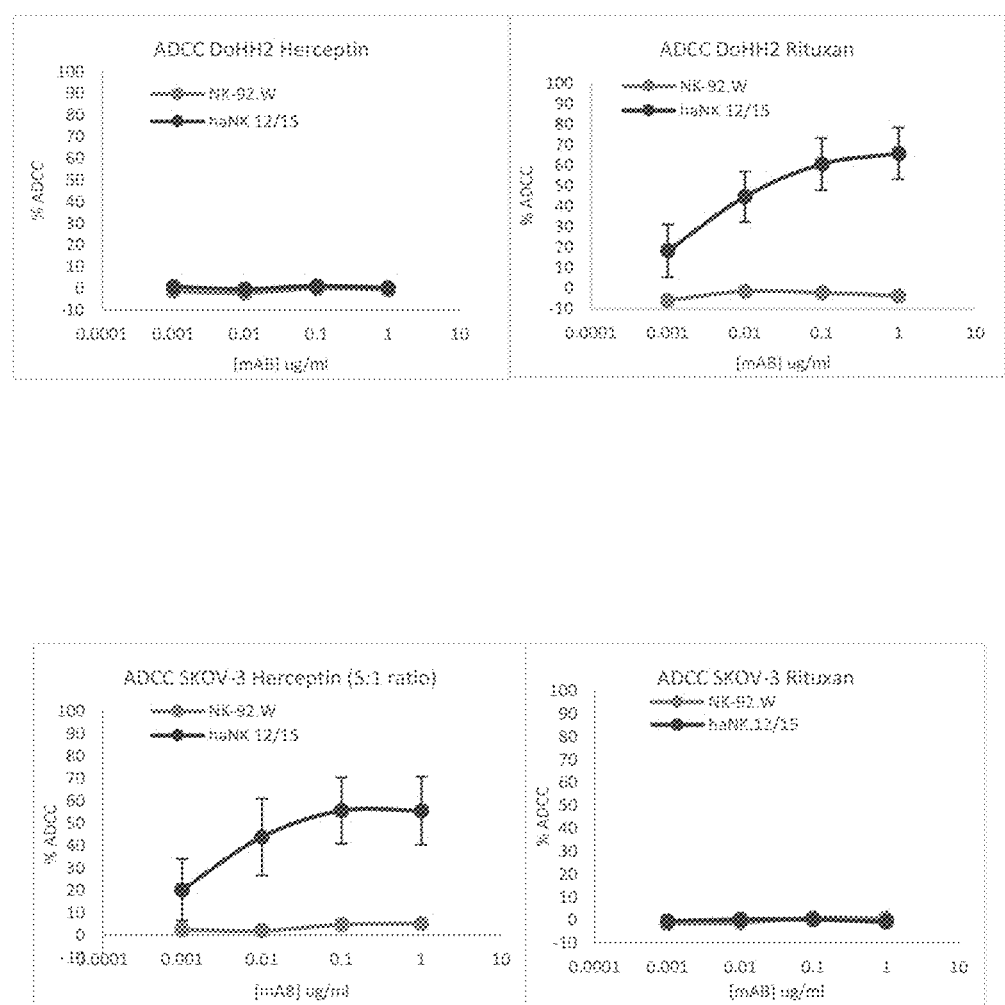
FIG. 4 provides illustrative data showing ADCC activity of CD16-expressing NK-92 cells used in combination with monoclonal antibodies.

ADCC activity was first tested against CD20+ cell line DoHH2 in combination with rituximab. The test was repeated over time (n=9), as well as against the Her2/Neu+ cell line SKOV3 in combination with Herceptin (n=5). The results are shown in FIG. 4. The modified NK-92.W cells that expressed CD16 and endoplasmic reticulum-targeted IL-2 (designated HaNK.12/15 in FIG. 4) showed enhanced ADCC activity towards SKOV-3 cells (FIG. 4, lower panel) when used with Herceptin, and ADCC activity towards DoHH2 cells (FIG. 4, upper panel) when used with rituximab. The haNK.12/15 cells did not show ADCC activity in the controls (DoHH2 cells, Herceptin antibody); SKOV-3 cells/rituximab). Unmodified NK-92.2 cells also did not show ADCC activity when administered with antibodies.

Examples 11-13 thus demonstrate that NK-92 cells that were modified to express CD16 and IL-2 using a plasmid vector exhibited enhanced ADCC activity when used in combination with a monoclonal antibody.

It is understood that the examples and embodiments described herein are for illustrative purposes only and that various modifications or changes in light thereof will be suggested to persons skilled in the art and are to be included within the spirit and purview of this application and scope of the appended claims. All publications, sequence accession numbers, patents, and patent applications cited herein are hereby incorporated by reference in their entirety for all purposes.

```
Illustrative Sequences
Low Affinity Immunoglobulin Gamma Fc Region Receptor III-A amino
acid sequence (mature form). The phenylalanine at position 158 is underlined
                                                             SEQ ID NO: 1
Arg Thr Glu Asp Leu Pro Lys Ala Val Val Phe Leu Glu Pro Gln Trp Tyr Arg Val Leu Glu Lys Asp Ser Val Thr Leu Lys Cys Gln Gly Ala Tyr Ser Pro Glu Asp Asn Ser Thr Gln Trp Phe His Asn Glu Ser Leu Ile Ser Ser Gln Ala Ser Ser Tyr Phe Ile Asp Ala Ala Thr Val Asp Asp Ser Gly Glu Tyr Arg Cys Gln Thr Asn Leu Ser Thr Leu Ser Asp Pro Val Gln Leu Glu Val His Ile Gly Trp Leu Leu Leu Gln Ala Pro Arg Trp Val Phe Lys Glu Glu Asp Pro Ile His Leu Arg Cys His Ser Trp Lys Asn Thr Ala Leu His Lys Val Thr Tyr Leu Gln Asn Gly Lys Gly Arg Lys Tyr Phe His His Asn Ser Asp Phe Tyr Ile Pro Lys Ala Thr Leu Lys Asp Ser Gly Ser Tyr Phe Cys Arg Gly Leu Phe Gly Ser Lys Asn Val Ser Ser Glu Thr Val Asn Ile Thr Ile Thr Gln Gly Leu Ala Val Ser Thr Ile Ser Ser Phe Phe Pro Pro Gly Tyr Gln Val Ser Phe Cys Leu Val Met Val Leu Leu Phe Ala Val Asp Thr Gly Leu Tyr Phe Ser Val Lys Thr Asn Ile Arg Ser Ser Thr Arg Asp Trp Lys Asp His Lys Phe Lys Trp Arg Lys Asp Pro Gln Asp Lys High Affinity Variant F158V Immunoglobulin Gamma Fc Region Receptor
III-A amino acid sequence (mature form). The valine at position 158 is underlined
                                                             SEQ ID NO: 2
Arg Thr Glu Asp Leu Pro Lys Ala Val Val Phe Leu Glu Pro Gln Trp Tyr Arg Val Leu Glu Lys Asp Ser Val Thr Leu Lys Cys Gln Gly Ala Tyr Ser Pro Glu Asp Asn Ser Thr Gln Trp Phe His Asn Glu Ser Leu Ile Ser Ser Gln Ala Ser Ser Tyr Phe Ile Asp Ala Ala Thr Val Asp Asp Ser Gly Glu Tyr Arg Cys Gln Thr Asn Leu Ser Thr Leu Ser Asp Pro Val Gln Leu Glu Val His Ile Gly Trp Leu Leu Leu Gln Ala Pro Arg Trp Val Phe Lys Glu Glu Asp Pro Ile His Leu Arg Cys His Ser Trp Lys Asn Thr Ala Leu His Lys Val Thr Tyr Leu Gln Asn Gly Lys Gly Arg Lys Tyr Phe His His Asn Ser Asp Phe Tyr Ile Pro Lys Ala Thr Leu Lys Asp Ser Gly Ser Tyr Phe Cys Arg Gly Leu Val Gly Ser Lys Asn Val Ser Ser Glu Thr Val Asn Ile Thr Ile Thr Gln Gly Leu Ala Val Ser Thr Ile Ser Ser Phe Phe Pro Pro Gly Tyr Gln Val Ser Phe Cys Leu Val Met Val Leu Leu Phe Ala Val Asp Thr Gly Leu Tyr Phe Ser Val Lys Thr Asn Ile Arg Ser Ser Thr Arg Asp Trp Lys Asp His Lys Phe Lys Trp Arg Lys Asp Pro Gln Asp Lys
```

-continued

Low Affinity Immunoglobulin Gamma Fc Region Receptor III-A amino acid sequence (precursor form). Position 176 of the precursor form corresponds to position 158 of the mature form. The Phe at position 176 is underlined

SEQ ID NO: 3

Met Trp Gln Leu Leu Leu Pro Thr Ala Leu Leu Leu Leu Val Ser Ala Gly Met Arg Thr Glu

Asp Leu Pro Lys Ala Val Val Phe Leu Glu Pro Gln Trp Tyr Arg Val Leu Glu Lys Asp Ser

Val Thr Leu Lys Cys Gln Gly Ala Tyr Ser Pro Glu Asp Asn Ser Thr Gln Trp Phe His Asn

Glu Ser Leu Ile Ser Ser Gln Ala Ser Ser Tyr Phe Ile Asp Ala Ala Thr Val Asp Asp Ser Gly

Glu Tyr Arg Cys Gln Thr Asn Leu Ser Thr Leu Ser Asp Pro Val Gln Leu Glu Val His Ile Gly

Trp Leu Leu Leu Gln Ala Pro Arg Trp Val Phe Lys Glu Glu Asp Pro Ile His Leu Arg Cys

His Ser Trp Lys Asn Thr Ala Leu His Lys Val Thr Tyr Leu Gln Asn Gly Lys Gly Arg Lys

Tyr Phe His His Asn Ser Asp Phe Tyr Ile Pro Lys Ala Thr Leu Lys Asp Ser Gly Ser Tyr Phe

Cys Arg Gly Leu <u>Phe</u> Gly Ser Lys Asn Val Ser Ser Glu Thr Val Asn Ile Thr Ile Thr Gln Gly

Leu Ala Val Ser Thr Ile Ser Ser Phe Phe Pro Pro Gly Tyr Gln Val Ser Phe Cys Leu Val Met

Val Leu Leu Phe Ala Val Asp Thr Gly Leu Tyr Phe Ser Val Lys Thr Asn Ile Arg Ser Ser Thr

Arg Asp Trp Lys Asp His Lys Phe Lys Trp Arg Lys Asp Pro Gln Asp Lys

High Affinity Variant Immunoglobulin Gamma Fc Region Receptor III-A amino acid sequence (precursor form). Position 176 of the precursor form corresponds to positions 158 of the mature form. The Val at position 176 is underlined

SEQ ID NO: 4

Met Trp Gln Leu Leu Leu Pro Thr Ala Leu Leu Leu Leu Val Ser Ala Gly Met Arg Thr Glu

Asp Leu Pro Lys Ala Val Val Phe Leu Glu Pro Gln Trp Tyr Arg Val Leu Glu Lys Asp Ser

Val Thr Leu Lys Cys Gln Gly Ala Tyr Ser Pro Glu Asp Asn Ser Thr Gln Trp Phe His Asn

Glu Ser Leu Ile Ser Ser Gln Ala Ser Ser Tyr Phe Ile Asp Ala Ala Thr Val Asp Asp Ser Gly

Glu Tyr Arg Cys Gln Thr Asn Leu Ser Thr Leu Ser Asp Pro Val Gln Leu Glu Val His Ile Gly

Trp Leu Leu Leu Gln Ala Pro Arg Trp Val Phe Lys Glu Glu Asp Pro Ile His Leu Arg Cys

His Ser Trp Lys Asn Thr Ala Leu His Lys Val Thr Tyr Leu Gln Asn Gly Lys Gly Arg Lys

Tyr Phe His His Asn Ser Asp Phe Tyr Ile Pro Lys Ala Thr Leu Lys Asp Ser Gly Ser Tyr Phe

Cys Arg Gly Leu <u>Val</u> Gly Ser Lys Asn Val Ser Ser Glu Thr Val Asn Ile Thr Ile Thr Gln Gly

Leu Ala Val Ser Thr Ile Ser Ser Phe Phe Pro Pro Gly Tyr Gln Val Ser Phe Cys Leu Val Met

Val Leu Leu Phe Ala Val Asp Thr Gly Leu Tyr Phe Ser Val Lys Thr Asn Ile Arg Ser Ser Thr

Arg Asp Trp Lys Asp His Lys Phe Lys Trp Arg Lys Asp Pro Gln Asp Lys

Polynucleotide Encoding the Low Affinity Immunoglobulin Gamma Fc Region Receptor III-A (Precursor) (Encodes phenylalanine at position 158)

SEQ ID NO: 5 atgtggcagc tgctcctccc aactgctctg ctacttctag tttcagctgg catgcggact gaagatctcc caaaggctgt ggtgttcctg gagcctcaat ggtacagggt gctcgagaag acagtgtga ctctgaagtg ccagggagcc tactcccctg aggacaattc cacacagtgg tttcacaatg agagcctcat ctcaagccag gcctcgagct acttcattga cgctgccaca gtcgacgaca gtggagagta caggtgccag acaaacctct ccaccctcag tgacccggtg cagctagaag tccatatcgg ctggctgttg ctccaggccc ctcggtgggt gttcaaggag aagacccta ttcacctgag gtgtcacagc tggaagaaca ctgctctgca taaggtcaca tatttacaga atggcaaagg caggaagtat ttcatcata attctgactt ctacattcca aaagccacac tcaaagacag cggctcctac ttctgcaggg ggcttttgg gagtaaaaat gtgtcttcag agactgtgaa catcaccatc actcaaggtt tggcagtgtc aaccatctca tcattctttc cacctgggta ccaagtctct ttctgcttgg tgatggtact cctttttgca gtggacacag gactatattt ctctgtgaag acaaacattc gaagctcaac aagagactgg aaggaccata aatttaaatg gagaaaggac cctcaagaca atga -continued Wild-Type IL-2
SEQ ID NO: 6
Met Tyr Arg Met Gln Leu Leu Ser Cys Ile Ala Leu Ser Leu Ala Leu Val Thr Asn Ser Ala Pro
Thr Ser Ser Ser Thr Lys Lys Thr Gln Leu Gln Leu Glu His Leu Leu Leu Asp Leu Gln Met Ile
Leu Asn Gly Ile Asn Asn Tyr Lys Asn Pro Lys Leu Thr Arg Met Leu Thr Phe Lys Phe Tyr
Met Pro Lys Lys Ala Thr Glu Leu Lys His Leu Gln Cys Leu Glu Glu Glu Leu Lys Pro Leu
Glu Glu Val Leu Asn Leu Ala Gln Ser Lys Asn Phe His Leu Arg Pro Arg Asp Leu Ile Ser
Asn Ile Asn Val Ile Val Leu Glu Leu Lys Gly Ser Glu Thr Thr Phe Met Cys Glu Tyr Ala Asp
Glu Thr Ala Thr Ile Val Glu Phe Leu Asn Arg Trp Ile Thr Phe Cys Gln Ser Ile Ile Ser Thr
Leu Thr IL-2-ER
SEQ ID NO: 7
Met Tyr Arg Met Gln Leu Leu Ser Cys Ile Ala Leu Ser Leu Ala Leu Val Thr Asn Ser Ala Pro
Thr Ser Ser Ser Thr Lys Lys Thr Gln Leu Gln Leu Glu His Leu Leu Leu Asp Leu Gln Met Ile
Leu Asn Gly Ile Asn Asn Tyr Lys Asn Pro Lys Leu Thr Arg Met Leu Thr Phe Lys Phe Tyr
Met Pro Lys Lys Ala Thr Glu Leu Lys His Leu Gln Cys Leu Glu Glu Glu Leu Lys Pro Leu
Glu Glu Val Leu Asn Leu Ala Gln Ser Lys Asn Phe His Leu Arg Pro Arg Asp Leu Ile Ser
Asn Ile Asn Val Ile Val Leu Glu Leu Lys Gly Ser Glu Thr Thr Phe Met Cys Glu Tyr Ala Asp
Glu Thr Ala Thr Ile Val Glu Phe Leu Asn Arg Trp Ile Thr Phe Cys Gln Ser Ile Ile Ser Thr
Leu Thr Gly Ser Glu Lys Asp Glu Leu

---

What is claimed is:

1. A cell line comprising engineered NK-92 cells genetically modified with a non-retroviral vector, wherein the engineered NK-92 cells comprise a bicistronic nucleic acid construct that comprises a polynucleotide that encodes a CD16 polypeptide having a valine at position 158 of the mature form of the CD16 polypeptide, and a polynucleotide that encodes an interleukin-2 (IL-2) polypeptide targeted to the endoplasmic reticulum (ER); and wherein genetic modification to obtain the engineered NK-92 cells comprises introducing the non-retroviral vector that comprises the bicistronic nucleic acid construct into NK-92 cells to be genetically modified.

2. The cell line of claim 1, wherein the non-retroviral vector is a plasmid vector.

3. The cell line of claim 1, wherein the CD16 polypeptide comprises an amino acid sequence having at least 90% identity to SEQ ID NO:2.

4. The cell line of claim 1, wherein the CD16 polypeptide comprises an amino acid sequence having at least 95% identity to SEQ ID NO:2.

5. The cell line of claim 1, wherein the CD16 polypeptide comprises the amino acid sequence of SEQ ID NO:2.

6. The cell line of claim 1, wherein the IL-2 polypeptide targeted to the ER comprises an amino acid sequence having at least 90% identity to SEQ ID NO:7.

7. The cell lines of claim 1, wherein the IL-2 polypeptide targeted to the ER comprises an amino acid sequence having at least 95% identity to SEQ ID NO:7.

8. The cell line of claim 1, wherein the IL-2 polypeptide targeted to the ER comprises the amino acid sequence of SEQ ID NO:7.

9. The cell line of claim 1, wherein the CD16 polypeptide comprises an amino acid sequence having at least 90% identity to SEQ ID NO:2; and the IL-2 polypeptide targeted to the ER comprises an amino acid sequence having at least 90% identity to SEQ ID NO:7.

10. The cell line of claim 1, wherein the CD16 polypeptide comprises an amino acid sequence having at least 95% identity to SEQ ID NO:2; and the IL-2 polypeptide targeted to the ER comprises an amino acid sequence having at least 95% identity to SEQ ID NO:7.

11. The cell line of claim 1, wherein the CD16 polypeptide comprises the amino acid sequence of SEQ ID NO:2; and the IL-2 polypeptide targeted to the ER comprises the amino acid sequence of SEQ ID NO:7.

* * * * *

UNITED STATES PATENT AND TRADEMARK OFFICE
CERTIFICATE OF CORRECTION

| | | |
|---|---|---|
| PATENT NO. | : 11,207,350 B2 | Page 1 of 1 |
| APPLICATION NO. | : 17/217839 | |
| DATED | : December 28, 2021 | |
| INVENTOR(S) | : Tien Lee et al. | |

It is certified that error appears in the above-identified patent and that said Letters Patent is hereby corrected as shown below:

On the Title Page

At item (72), please add inventor --Kerry Campbell, Wyncote, PA (US)--

Signed and Sealed this
Twenty-eighth Day of November, 2023

*Katherine Kelly Vidal*

Katherine Kelly Vidal
*Director of the United States Patent and Trademark Office*